US010092269B2

United States Patent
Shams et al.

(10) Patent No.: US 10,092,269 B2
(45) Date of Patent: Oct. 9, 2018

(54) INFRASONIC STETHOSCOPE FOR MONITORING PHYSIOLOGICAL PROCESSES

(71) Applicant: The United States of America as represented by the Administrator of the National Aeronautics and Space Administration, Washington, DC (US)

(72) Inventors: Qamar A. Shams, Yorktown, VA (US); Allan J. Zuckerwar, Williamsburg, VA (US); Albert L. Dimarcantonio, Williamsburg, VA (US)

(73) Assignee: The United States of America as represented by the Administrator of NASA, Washington, DC (US)

( * ) Notice: Subject to any disclaimer, the term of this patent is extended or adjusted under 35 U.S.C. 154(b) by 0 days.

(21) Appl. No.: 15/515,670

(22) PCT Filed: Mar. 17, 2015

(86) PCT No.: PCT/US2015/020964
§ 371 (c)(1),
(2) Date: Mar. 30, 2017

(87) PCT Pub. No.: WO2016/053380
PCT Pub. Date: Apr. 7, 2016

(65) Prior Publication Data
US 2017/0296138 A1 Oct. 19, 2017

Related U.S. Application Data

(63) Continuation of application No. 14/658,584, filed on Mar. 16, 2015, now Pat. No. 9,445,779.
(Continued)

(51) Int. Cl.
*A61B 7/04* (2006.01)
*A61B 8/08* (2006.01)
(Continued)

(52) U.S. Cl.
CPC ............ *A61B 7/04* (2013.01); *A61B 5/02411* (2013.01); *A61B 5/117* (2013.01); *A61B 5/164* (2013.01);
(Continued)

(58) Field of Classification Search
CPC .......... A61B 7/04; A61B 8/0883; H04R 1/08; H04R 2410/00
See application file for complete search history.

(56) References Cited

U.S. PATENT DOCUMENTS 3,247,324 A * 4/1966 Cefaly ..................... A61B 7/02
181/131
3,550,720 A * 12/1970 Ballard .................. H04R 1/086
181/175
(Continued)

FOREIGN PATENT DOCUMENTS

CN 2065053 11/1990
CN 102475550A A 5/2012

OTHER PUBLICATIONS

John G. Webster, Medical Instrumentation Application and Design, Fourth Edition, 2010, pp. 308-311, John Wiley & Sons, Inc. New Jersey.
(Continued)

*Primary Examiner* — Brenda C Bernardi
(74) *Attorney, Agent, or Firm* — Andrea Z. Warmbier; Robin W. Edwards; Mark P. Dvorscak

(57) ABSTRACT

An infrasonic stethoscope for monitoring physiological processes of a patient includes a microphone capable of detecting acoustic signals in the audible frequency bandwidth and in the infrasonic bandwidth (0.03 to 1000 Hertz), a body coupler attached to the body at a first opening in the microphone, a flexible tube attached to the body at a second opening in the microphone, and an earpiece attached to the flexible tube. The body coupler is capable of engagement
(Continued)

with a patient to transmit sounds from the person, to the microphone and then to the earpiece.

20 Claims, 17 Drawing Sheets

Related U.S. Application Data

(60) Provisional application No. 62/058,794, filed on Oct. 2, 2014.

(51) Int. Cl.
    *A61B 7/02* (2006.01)
    *H04R 1/46* (2006.01)
    *A61B 5/024* (2006.01)
    *A61B 5/117* (2016.01)
    *A61B 5/16* (2006.01)
    *A61B 5/00* (2006.01)
    *A61B 8/00* (2006.01)

(52) U.S. Cl.
    CPC .......... *A61B 5/4362* (2013.01); *A61B 7/023* (2013.01); *A61B 7/026* (2013.01); *A61B 8/0866* (2013.01); *A61B 8/0883* (2013.01); *A61B 8/488* (2013.01); *A61B 8/5207* (2013.01); *A61B 8/565* (2013.01); *H04R 1/46* (2013.01)

(56) References Cited

U.S. PATENT DOCUMENTS

| | | | | |
|---|---|---|---|---|
| 4,281,222 A * | 7/1981 | Nakagawa | ........... | H04R 19/016 381/174 |
| 4,625,827 A * | 12/1986 | Bartlett | ........... | H04R 1/086 181/158 |
| 4,712,429 A * | 12/1987 | Raspet | ........... | G01H 3/00 181/175 |
| 5,003,605 A * | 3/1991 | Phillipps | ........... | A61B 5/04085 381/67 |
| 5,195,843 A * | 3/1993 | George | ........... | C04B 38/00 405/63 |
| 5,226,076 A * | 7/1993 | Baumhauer, Jr. | ........ | H04M 1/19 379/419 |
| 5,349,140 A * | 9/1994 | Valenzin | ........... | H04R 1/086 181/158 |
| 5,394,880 A * | 3/1995 | Atlee, III | ........... | A61B 5/0421 600/528 |
| 5,511,130 A * | 4/1996 | Bartlett | ........... | H04M 1/19 381/170 |
| 5,650,598 A * | 7/1997 | Abelson | ........... | A61B 7/02 181/131 |
| 5,684,324 A * | 11/1997 | Bernstein | ........... | G01H 11/06 257/415 |
| 5,790,679 A * | 8/1998 | Hawker | ........... | H04M 1/0202 379/388.02 |
| 6,091,829 A * | 7/2000 | Blackmer | ........... | H04R 1/083 381/345 |
| 6,108,415 A * | 8/2000 | Andrea | ........... | H04M 1/19 379/433.03 |
| 6,284,360 B1 * | 9/2001 | Johnson | ........... | B32B 27/08 428/317.7 |
| 6,570,500 B1 * | 5/2003 | Pieper | ........... | G08B 13/1681 340/541 |
| 6,626,822 B1 * | 9/2003 | Jaeger | ........... | H04R 25/606 381/326 |
| 6,788,417 B1 * | 9/2004 | Zumberge | ........... | G01H 9/004 356/477 |
| 6,831,978 B2 * | 12/2004 | Vandivier | ........... | H04M 1/6075 379/420.03 |
| 6,928,174 B1 | 8/2005 | Mantysalo et al. | | |
| 6,975,736 B2 * | 12/2005 | Hasegawa | ........... | H04R 19/04 381/174 |
| 7,065,224 B2 * | 6/2006 | Cornelius | ........... | H04R 19/04 181/158 |
| 7,110,553 B1 * | 9/2006 | Julstrom | ........... | H04R 3/005 381/356 |
| 8,401,217 B2 | 3/2013 | Shams et al. | | |
| 8,671,763 B2 * | 3/2014 | Zuckerwar | ........... | G01H 11/06 73/649 |
| 2003/0055359 A1 * | 3/2003 | Halleck | ........... | A61B 7/003 600/586 |
| 2005/0025328 A1 * | 2/2005 | Song | ........... | H04R 19/016 381/369 |
| 2006/0167385 A1 * | 7/2006 | Guion | ........... | A61B 7/00 600/586 |
| 2006/9167385 | 7/2006 | Guion | | |
| 2007/0003092 A1 * | 1/2007 | Shen | ........... | A42B 1/068 381/374 |
| 2007/0053538 A1 * | 3/2007 | Jensen | ........... | H04R 1/086 381/359 |
| 2008/0232605 A1 * | 9/2008 | Bagha | ........... | A61B 7/04 381/67 |
| 2009/0022341 A1 * | 1/2009 | Shams | ........... | G01H 11/02 381/174 |
| 2009/0211838 A1 * | 8/2009 | Bilan | ........... | A61B 7/04 181/131 |
| 2012/0302920 A1 * | 11/2012 | Bridger | ........... | A61B 7/04 600/586 |
| 2013/0028433 A1 * | 1/2013 | Smith | ........... | A61B 7/04 381/67 |
| 2013/0150744 A1 * | 6/2013 | Brattain | ........... | A61B 5/4848 600/529 |
| 2014/0212863 A1 * | 7/2014 | Lowe | ........... | B29C 45/14 434/267 |

OTHER PUBLICATIONS

Dominic Basulto, "The heartbeat vs the fingerprint in the battle for biometric authentication," Washington Post, accessed online at http://www.washingtonpost.com/blogs/innovations/wp/2014/11/21/the-heartbeat-vs-the-fingerprint-in-the-battle-for-biometric-authentication, Nov. 21, 2014.
Qamar A. Shams, et al , "Compact Nonporous Windscreen for Infrasonic Measurements". J. Acoust. Soc. Am., Sep. 2005, 118(3) Pt. 1, pp. 1335-1340.
NASA Langley Research Center, Hampton, VA, Sep. 1, 2005, Compact Infrasonic Windscreen—High Values of Infrasound-Transmission and Wind-Noise-Attenuation Coefficients can be realized.
PCT International Search Report PCT/US2015/020964, pp. 1-15, dated Jun. 29, 2015.
Jamar, Kyle, et al., "Electronic Stethoscope," University of Wisconsin—Madison: Department of Biomedical Engineering, Oct. 26, 2011, pp. 1-18.
Written Opinion Intellectual Property Office of Singapore 11201702444P, pp. 1-5, dated Apr. 23, 2018.
Search Report Intellectual Property Office of Singapore 11201702444P, pp. 1-3, dated Apr. 19, 2018.

* cited by examiner

INFRASONIC STETHOSCOPE FOR MONITORING PHYSIOLOGICAL PROCESSES

CROSS-REFERENCE TO RELATED PATENT APPLICATION(S)

This application is being filed as the national stage patent application of PCT International Patent Application No. PCT US2015/020964, filed on 17 Mar. 2015, which claims the benefit of and priority to U.S. Non-Provisional patent application Ser. No. 14/658,584, filed on Mar. 16, 2015, which claims the benefit of and priority to U.S. Provisional Patent Application Ser. No. 62/058,794, filed on Oct. 2, 2014, the contents of which are incorporated by reference herein in their entirety.

STATEMENT REGARDING FEDERALLY SPONSORED RESEARCH OR DEVELOPMENT

The invention described herein was made in the performance of work under a NASA contract and by employees of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor elected not to retain title.

FIELD OF THE INVENTION

The present disclosure relates to an infrasonic stethoscope (or "infrascope") for monitoring physiological processes and is particularly related to a wireless infrasonic stethoscope.

BACKGROUND OF THE INVENTION

Sound at frequencies below 20 Hertz is termed "infrasound." A particularly favorable property of infrasound is its propagation over long distances with little attenuation. Infrasound has this property because atmospheric absorption is practically negligible at infrasonic frequencies, and because there is an acoustic "ceiling" in the stratosphere where a positive gradient of the speed of sound versus altitude causes reflections of infrasonic rays back to Earth. Infrasound propagation over long distances (e.g., thousands of kilometers) is predominantly due to refractive ducting from the upper layers in the atmosphere, while propagation over short distances is completed by direct path.

The density, acoustic impedance, and speed of sound through different human and animal tissues varies depending upon location of the auscultation. When an acoustic signal travels through tissue layers, the amplitude of the original signal becomes more attenuated with depth of the acoustic signal source. Attenuation (i.e. energy loss) could be due to absorption, reflection, and scattering at interfaces of different tissues. The degree of attenuation also depend upon frequency of the sound wave and the distance it travels. Generally speaking, a high frequency acoustic signal is associated with high attenuation thus limiting tissue penetration, but lower frequencies do not have attenuation issue thus providing physicians better understanding of the heart performance. More than 60% power spectral density of heart signals fall in infrasonic bandwidth. Low frequency acoustic signals detected from different human organs, such as the heart, are valuable to physicians for monitoring heart and lungs.

Microphones and stethoscopes are regularly used by physicians in detecting sounds for monitoring physiological conditions. Phonocardiography has been in use for more than 75 years to monitor heart beats as well as to detect the audible sound of the blood flowing through the heart. These physiological condition monitors are coupled directly to a person's body and processes are measured either by listening or by recording the signals in certain bandwidth. The physiological processes such as respiration and cardiac activity are reflected in a different frequency bandwidth from 1/10 Hertz to 500 Hertz. Other stethoscopes are capable of monitoring only audible frequency bandwidth, and are not capable of monitoring infrasonic frequencies below 20 Hz. Low frequency acoustic signals below 20 Hertz are not audible, but can provide useful information to physicians.

Inside of a normal heart, there are four chambers namely; the right atrium, the left atrium, the right ventricle, and the left ventricle. The function of a heart is to keep blood flowing in one-way direction. When a valve opens, the valve lets the right amount of blood through, and then closes to keep blood from flowing backwards in between beats. An easy and relatively inexpensive assessment of any patient's cardiac status can be determined by sounds in the chest. The key to good auscultation lies in low and high pitched sounds. As the heart, beats, blood flows from right atrium into the right ventricle through the tricuspid valve.

Blood then flows to the lungs through pulmonary valve (sometimes also called semilunar valve) to pick up right amount of oxygen. The blood flows from the lungs back into the left atrium and enters into the left ventricle through the mitral valve. Blood then is pumped to the aorta through the aortic valve and goes out to rest of the body providing oxygen and nutrients to the body cells. All four chambers (right atrium, right ventricle, left atrium, and left ventricle) must contract at just the right time for normal heart to functioning properly. The proper timing is coordinated by heart's electrical pathways. The electrical signals are produced by the sinoatrial node (SA node) and atrioventricular node (AV node).

The SA node is a group of cells located in the right atrium that initiates contraction of both atria to push blood into their corresponding ventricles. Due to insulation between the atria and ventricles, the SA node signals do not continue directly to the ventricles but pass through the AV node, which is another group of cells located in the floor of right atrium between the atria and ventricles. The AV node regulates the signal to ensure that the atria are empty and closed before the ventricles contract to push the blood out of the heart. The SA node sends signals to stimulate the heart to beat between 60-100 times per minute.

The cardiovascular system is complex and numerous problems could take place inside anywhere from the electrical system of the heart to the large or small blood vessels. There are over 60 different types of cardiovascular disease, all of which somehow affect the cardio or vascular systems. The heart sounds generated by the beating of heart and the resultant flow of blood can provide important information about the condition of the heart. In healthy adults, two normal heart sounds occur in sequence with the heartbeat. A first sound is produced based on the closure of the atrioventricular valves (i.e. mitral and tricuspid valves) located between the atria and ventricles, and is referred to as S1. A second sound is produced as a result of closure of the semilunar valves (i.e. pulmonary and aortic valves), which control the flow of blood as it leaves the heart via the arteries, and is referred to as S2.

The first heart sound S1 consists of four sequential components: 1. Small low frequency vibrations that coincide with the beginning of left ventricular contraction. 2. High frequency vibration, easily audible related to mitral valve closure (M1). 3. A second high frequency component related to tricuspid valve closure. 4. Small frequency vibrations that coincide with the acceleration of blood into great vessel.

In addition to these normal sounds, a variety of other sounds may be present but requires highly sensitive microphone with lowest acoustic background noise level along with filters to pick up these sounds. A third low frequency sound, which may be heard at the beginning of the diastole, is referred to as S3. A fourth sound may be heard in late diastole during atrial contraction, is referred to as S4. These sounds can be associated with heart murmurs, adventitious sound, ventricular gallop and gallop rhythms. The S4 provides information about hypertension and acute myocardial infarction.

The cardiac sounds S1, S2, S3, and S4 can be attributed to specific cardiac activity. S1 is attributed to the onset of the ventricular contraction (10-140 Hertz bands), S2 is attributed to closure of the semilunar valves (10-400 Hertz bands). S3 may be attributed to ventricular gallop, which may be heard during rapid filling (i.e. diastole) of the ventricles. S4 may be attributed to atrial gallop, which may be heard in late diastole, during atrial contraction. S3 and S4 are of very low intensity and can be heard externally when amplified.

Other sounds may be heard from opening snaps of the mitral valve or ejection sound of the blood in the aorta which indicates valve malfunctions, such as stenosis or regurgitation. Other high frequency murmurs can occur between the two major heart sounds during systole or diastole. The murmurs can be innocent but can also indicate certain cardiovascular defects.

Continuous fetal heart monitoring is an important step to evaluate the well-being of a fetus. The fetal heart rate may indicate if the fetus is getting enough oxygen. Most of the time ultrasound transducers are used for monitoring fetal heart rate as conventional stethoscopes undesirably pick up signals from maternal abdominal vessels. Due to abdominal fat of the mother or fetal positioning, it may be difficult to monitor fetal heart passively, so most of the time ultrasound transducers are used where ultrasound pulses are radiated towards the fetus and reflective pulses are used for monitoring. If enough reflective signals are not received, the penetration depth of ultrasound pulses are increased which may decrease quality and signal-to-noise ratio. The high frequency ultrasound signals become attenuated due to absorption, reflection, and scattering due to abdominal fat. The infrasound signals have relatively very low attenuation coefficient hence the signals are expected to be of high quality with better signal to noise ratio and helpful to gynecologists.

Many heart sounds are in a low-frequency band spectrum with low intensity level and may require extremely sensitive infrasonic microphone to acquire useful information that cannot be perceived by the physician's ear. The passive filtering may be useful to record low and high frequency bands separately. The sounds are of short duration and highly non-stationary but enable to measuring systolic and diastolic time intervals, which may have diagnostic importance.

Accordingly, there is a need for a monitoring device that overcomes the disadvantages presented by the prior art.

BRIEF SUMMARY OF THE INVENTION

An infrasonic stethoscope (or infrascope) or monitoring physiological processes of a patient includes a microphone capable of detecting acoustic signals in the audible frequency bandwidth and in the infrasonic bandwidth. The microphone has a body, which includes first and second spaced apart openings. A body coupler is attached to the first opening of the body to form a substantially air-tight seal, wherein the body coupler is capable of engagement with the patient to monitor physiological processes. A flexible tube is attached to the body at the second opening in the microphone. An earpiece is attached to the flexible tube. The body coupler is capable of engagement with a patient to transmit sounds from the patient to the microphone, and then to the earpiece.

These and other features, advantages, and objects of the present invention will be further understood and appreciated by those skilled in the art by reference to the following specification, claims, and appended drawings.

BRIEF DESCRIPTION OF THE SEVERAL VIEWS OF THE DRAWINGS

The organization and manner of the structure and operation of the disclosed embodiments, together with further objects and advantages thereof, may best be understood by reference to the following description, taken in connection with the accompanying drawings, which are not necessarily drawn to scale, wherein like reference numerals identify like elements in which.

DETAILED DESCRIPTION OF THE INVENTION

Figure 1:
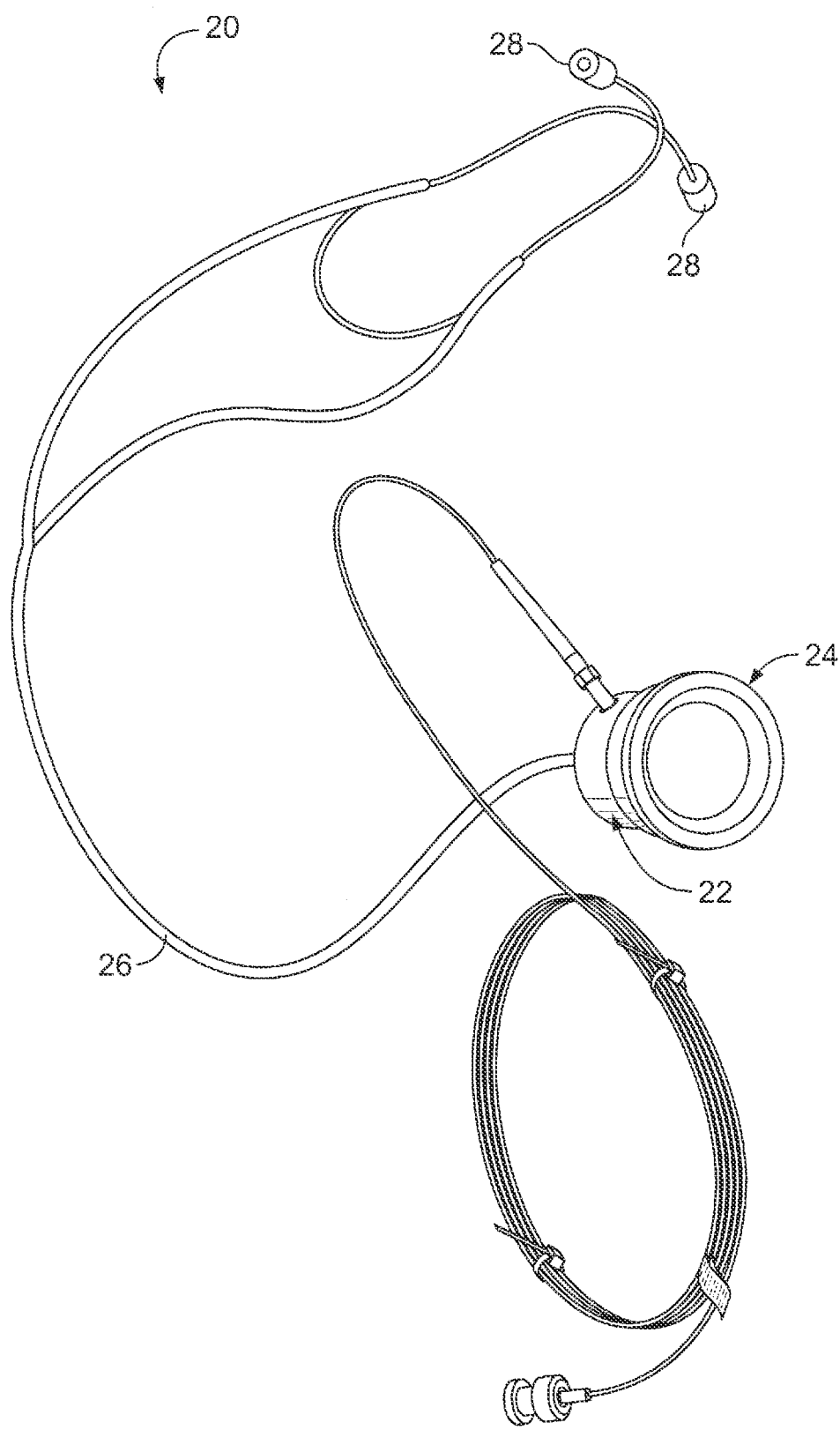
FIG. 1 is perspective view of an embodiment of an infrascope which can be used for external monitoring of a patient.

While the disclosure may be susceptible to embodiment in different forms, there is shown in the drawings, and herein will be described in detail, a specific embodiment with the understanding that the present disclosure is to be considered an exemplification of the principles of the disclosure, and is not intended to limit the disclosure to that as illustrated and described herein. Therefore, unless otherwise noted, features disclosed herein may be combined together to form additional combinations that were not otherwise shown for purposes of brevity. It will be further appreciated that in some embodiments, one or more elements illustrated by way of example in a drawing(s) may be eliminated and/or substituted with alternative elements within the scope of the disclosure.

Figure 4:
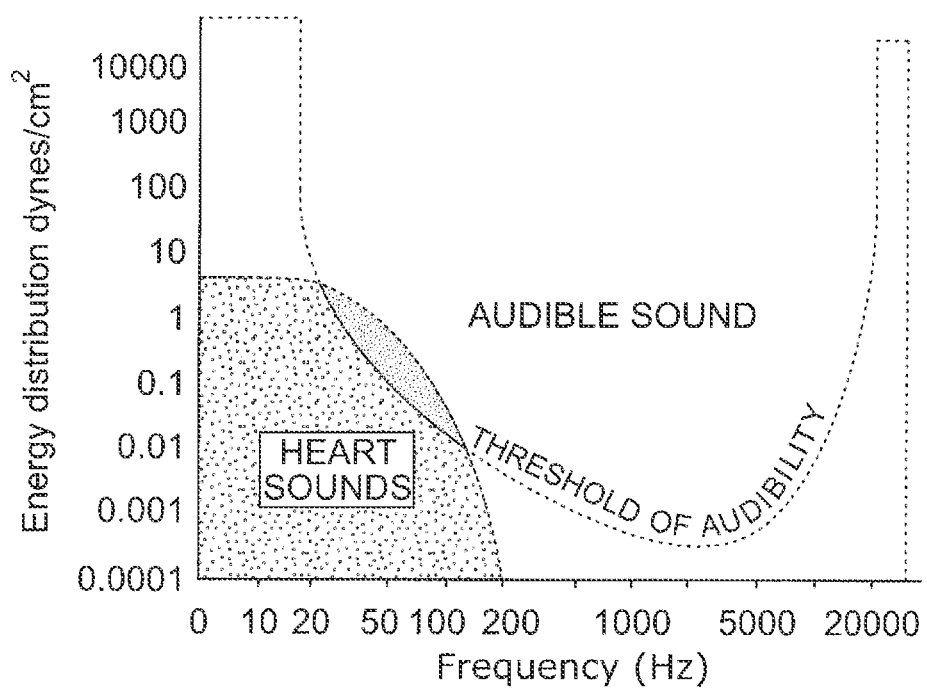
FIG. 4 is a graph showing, bandwidths of heart sound.

As shown in FIG. 1, an infrascope 20 is provided to monitor physiological processes of a patient. The infrascope 20 detects signals in a bandwidth from 0.03 Hertz through 1000 Hertz, or alternatively 0.03 through 500 Hertz. These bandwidths contains signals which are audible and inaudible to the human ear. The infrascope 20 has multiple applications to measure a variety of human physiological processes, including, but not limited to, cardiac monitoring, external fetal monitoring, internal fetal monitoring, stress phonocardiography testing, Doppler phonocardiography, biometric identification and polygraphs. The bandwidth of audible and inaudible sounds produced by cardiac activity are shown in FIG. 4, which demonstrates energy distribution (dynes/cm$^2$) as a function of frequency (Hz).

Figure 2:
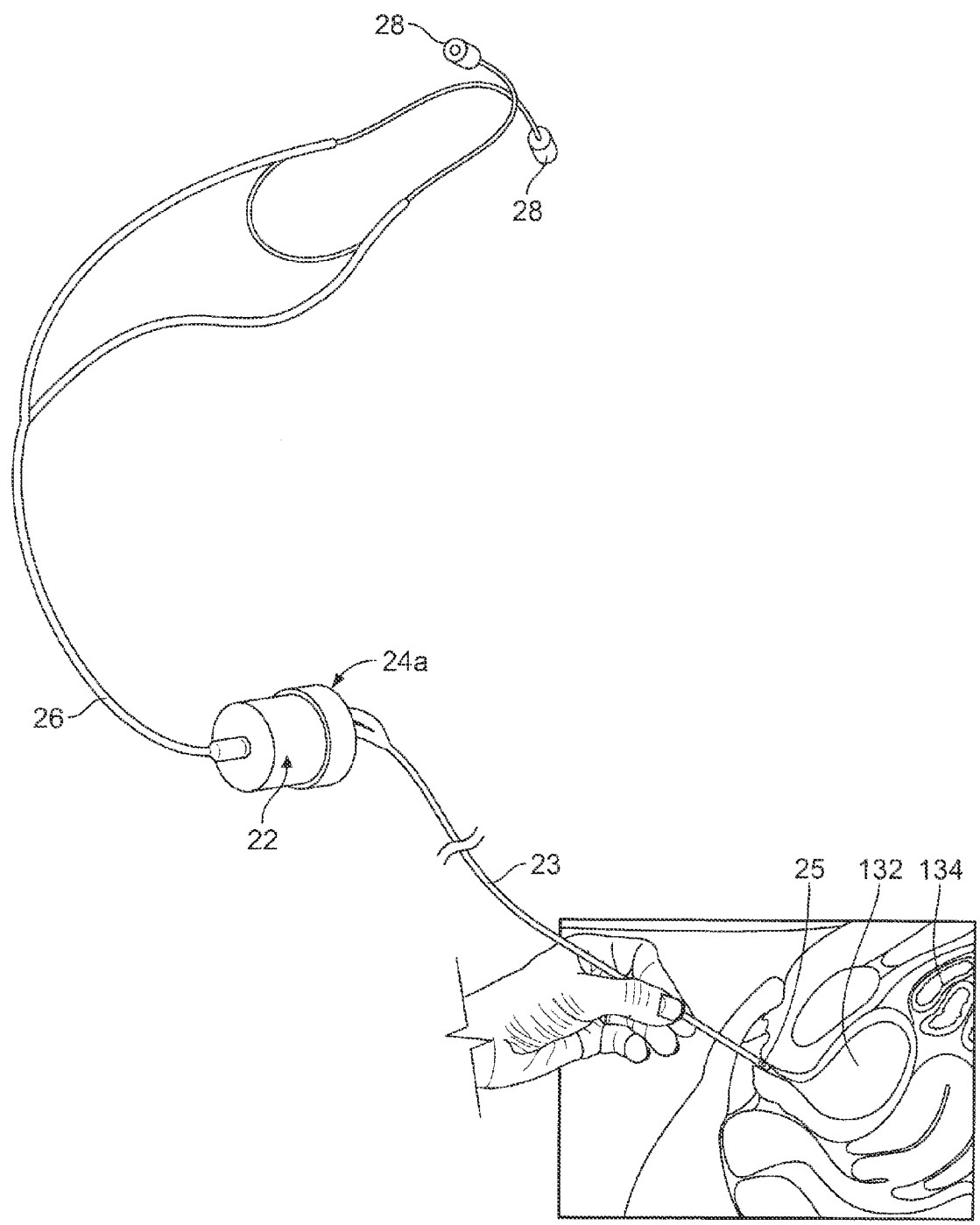
FIG. 2 is a perspective view of the infrascope attached to a catheter, for use in internal fetal monitoring of a patient.

The infrascope 20 contains a microphone 22, a body coupler 24 or 24a attached to the microphone 22, a flexible tube 26 attached to the microphone 22 and earpiece 28 connected to the flexible tube 26. For internal fetal monitoring, as shown in FIG. 2 and as further described herein, the body coupler 24a is used and the microphone 22 is further connected to a catheter 23 via the body coupler 24a.

The microphone 22 is substantially the same as the microphone described in U.S. Pat. No. 8,401,217, with the modifications described herein. The contents of U.S. Pat. No. 8,401,217 is incorporated by reference in its entirety.

Figure 5:
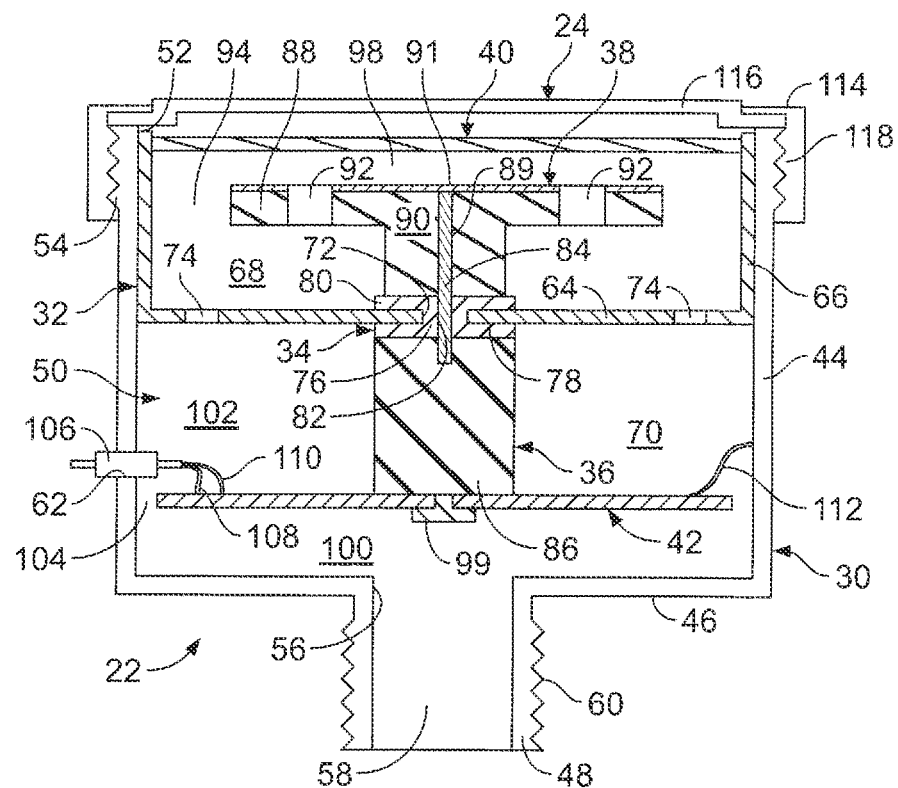
FIG. 5 is a cross-sectional view of a microphone which forms part of an infrascope of the present invention and of a body coupler according to a first embodiment attached to the microphone and which forms part of the infrascope of the present disclosure.

The microphone 22 is best shown in FIG. 5 and includes a cup-like body 30, a cup-like support plate 32, an insulating member 34, a conductor 36, a backplate 38, a membrane 40 and a low-noise preamplifier board 42.

The body 30 has a cylindrical side wall 44 having a proximal end and a distal end, an end wall 46 at the proximal end of the body 30, and a connection port 48 extending proximally from the end wall 46. The body 30 is formed of metal, such as a stainless steel or aluminum. The side wall 44 and the end wall 46 define an internal cavity 50 within the body 30. The distal end of the body 30 is open such that an aperture 52 is defined in the body 30. A thread form 54 is provided on the exterior surface of the side wall 44 at the distal end. The end wall 46 substantially closes the proximal end of the body 30, with the exception of an aperture 56 therethrough, and may extend perpendicularly relative to the side wall 44. The aperture 56 may be centrally located in the end wall 46 and is communication with the connection port 48. The connection port 48 extends proximally from the end wall 46 and has a passageway 58 therethrough which is communication with the cavity 50 via the aperture 56. The exterior surface of the connection port 48 has a thread form 60 thereon. An aperture 62 is provided through the side wall 44 at a position spaced from the proximal end of the side wall 44.

The support plate 32 is attached to the internal surface of the side wall 44 and seats within the cavity 50. The support plate 32 is formed of metal, and has a circular base wall 64 which spans the diameter of the side wall 44 and is parallel to the end wall 46, and a depending side wall 66 which extends distally from the base wall 64. The side wall 66 terminates in a free end. The side wall 66 engages against the internal surface of the side wall 44 of the body 30, such that the free end of the side wall 66 is proximate to the distal end of the body 30, and the base wall 64 is spaced from the distal end of the body 30. The support plate 32 is affixed to the body 30 by suitable means, such as welding, in such a way that whole assembly can be connected to the ground of preamplifier board 42. As a result of this arrangement, a distal chamber 68 is formed between the base wall 64 and the distal end of the body 30, and a proximal chamber 70 is formed between the base wall 64 and the proximal end of the body 30. The base wall 64 has an aperture 72 therethrough, which may be centrally located. The base wall 64 also has at least one aperture 74 or slot therethrough to allow air to flow from the distal chamber 68 to the proximal chamber 70.

The insulating member 34, which may be formed of plastic, ceramic, wood or any suitable insulating material, seats within the aperture 72 in the support plate 32 and is used to electrically isolate the conductor 36, the backplate 38 and the preamplifier board 42 from the support plate 32. As shown, the insulating member 34 has a central portion 76 which extends through the aperture 72, a proximal portion 78 which extends radially outwardly from the central portion 76 on the distal side of the base wall 64, and a distal portion 80 which extends radially outwardly from the central portion 76 on the proximal side of the base wall 64. A passageway 82 extends through the central portion 76.

The backplate 38 is formed of a conducting material, and is formed from a base wall 88 and may further be formed of a proximal extending portion 90 which extends perpendicularly from the base wall 88. The backplate 38 may be formed of, for example, from conducting ceramics, brass, or stainless steel. A passageway 89 extends through the base wall 88, and extending portion 90 if provided, from its proximal surface to its distal surface. A permanently polarized thin polymer film 91 is coated on the distal surface of the backplate 38. The polarized thin polymer film 91 operates without the need for an external power supply. As described in U.S. Pat. No. 8,401,217, the backplate 38 has a plurality of spaced apart holes 92 therethrough (two holes are visible in FIG. 5. The extending portion 90 engages against the distal portion 80 of the insulating member 34, and is secured to a distal end of the conductor 36, such that the backplate 38 and the conductor 36 are in electrical communication. The base wall 88 of the backplate 38 is parallel to the base wall 64 of the support plate 32. A slot 94 is defined between the outer diameter of the backplate 38 and the side wall 44 of the body 30. The area between the backplate 38 and the proximal end of the body 30 defines a backchamber.

The conductor 36 extends through the passageways 82, 89 and extends into the proximal chamber 70. The conductor 36 is electrically connected to backplate 38. As shown, the conductor 36 is formed of a conducting rod or wire 84 which extends through the passageways 82, 89, and a conductive rod 86 extending proximally from the conducting rod or wire 84 and the insulating member 34. If formed of two components, the components are suitably connected to each other to form an electrical connection. The rod or wire 84 and rod 86 may be formed of brass, or may be formed of differing conductive materials. The proximal end of the conductor 46 is proximate, to but spaced from, the end wall 46 such that a gap is defined therebetween.

The membrane 40 is formed of a flexible conductive material and is seated at the distal free end of the side wall 66 of the support plate 32 such that the membrane 40 is positioned within the distal chamber 68 and is proximate to, but spaced from, the distal end of the body 30. The diameter of the membrane 40 is selected so that the membrane 40 stays within side wall 66. The membrane 40 is parallel to the end wall 46 of the body 30 and to the base wall 64 of the support plate 32. As a result, the membrane 40 is in electrical communication with the support plate 32. The tension of the membrane 40 may be less than about 400 Newton per meter.

The backplate 38 is proximate to, but spaced from the membrane 40, such that an air gap 98 is formed between the membrane 40 and the backplate 38 to create a capacitor in the microphone 22 as is described in U.S. Pat. No. 8,401,217. As described in U.S. Pat. No. 8,401,217, the number, locations and sizes of the holes 92, the size of the slot 94, and the inner volume of the backchamber are selected such to allow enough air flow to provide proper damping of the motion of the membrane 40. As described in U.S. Pat. No. 8,401,217, the backchamber serves as a reservoir for the airflow through the holes 92 in the backplate.

In an exemplary embodiment, the membrane 40 has a diameter of approximately 1.05 inches (0.0268 meter). The membrane 40 may have the following characteristics/dimensions:
- radius=0.0134 meter;
- thickness=$2.54 \times 10^{-5}$ meter;
- density=8000 kilogram/meter$^3$;
- tension=400 N/meter;
- surface density=0.1780 kilogram/meter$^2$; and
- stress=47.4045 PSI.

The microphone 22 may comprises an air layer which may have the following characteristics/dimensions:
- air gap=$2.54 \times 10^{-5}$ meter;
- density=1.2050 kilogram/meter$^3$;
- viscosity=$1.8 \times 10^{-5}$ Pascal-second;
- sound velocity through the air gap=290.2 meters per second; and
- gamma=1.4

The microphone 22 may also comprise a slot 94 which may have the following characteristics/dimensions:
- distance from the center of the backplate=0.0117 meter;
- width=0.00351 meter;
- depth=0.00114 meter; and
- area=0.000258 meter$^2$.

The backplate 38 may define six holes 92, and each hole 92 may have the following characteristics/dimensions:
- distance from center of backplate to center of hole=0.00526 meter;
- radius=0.002 meter;
- depth=0.045 meter;
- angle between two lines going from center of backplate to either side edge of hole=43.5 degrees; and
- area=$1.26 \times 10^{-5}$ meter$^2$.

The microphone 22 may also have the following further characteristics/dimensions:
- volume of the backchamber=$5 \times 10^{-5}$ meter$^3$;
- membrane mass=480 kilogram/meter$^4$;
- membrane compliance=$3.2 \times 10^{-11}$ meter$^5$/Newton; and
- air gap compliance=$3.5 \times 10^{10}$ meter$^5$/Newton.

In one embodiment, the resonant frequency of the microphone 22 may be 3108.01 Hertz.

The preamplifier board 42 is planar and extends radially outwardly from the proximal end of the conductor 36. The preamplifier board 42 is connected to the proximal end of the conductor 36 by suitable means such that there is an electrical connection between the preamplifier board 42 and the conductor 36, such as a brass screw 99. The preamplifier board 42 is parallel to the end wall 36 of the body 30, the base wall 64 of the support plate 32 and the base wall 88 of the backplate 38. The position of the preamplifier board 42 defines a first proximal chamber 100 which has a volume V1 between the preamplifier board 42 and the end wall 46 of the body 30, and a second distal chamber 102 which has a volume V2 between the preamplifier board 42 and the base wall 64 of the support plate 32. A slot 104 is defined between the outer diameter of the preamplifier board 42 and the side wall 44 of the body 30 to allow air to flow from the distal chamber 102 to the proximal chamber 100. In an embodiment, volume V1 is approximately 0.1287 cubic inch, and volume V2 is approximately 0.6 cubic inch. The air can only flow from the distal chamber 102 to the proximal chamber 100 through the slot 104. In an embodiment, this slot 104 has a clearance distance between the outer diameter of the preamplifier board 42 and the side wall 44 of approximately 0.025", which slot 104 extends around the preamplifier board 42.

An electrical connection 106 extends through the aperture 62 in the side wall 44 and is sealed to the side wall 44 by suitable means. The electrical connection 106 is electrical communication with the preamplifier board 42 via wires 108, 110. The preamplifier board 42 is also electrically connected to the body 30 via a wire 110, which provides a ground to the preamplifier board 42. The preamplifier board 42 contains known components for measuring the capacitance between the membrane 40 and the backplate 38, and converting this measured capacitance into voltage.

The connection port 48 is connected to a distal end of the flexible tube 26, which may be formed of latex or rubber, which has an earpiece 28 at the proximal end of the tube 26. Such a flexible tube 26 and earpiece 28, like a typical stethoscope, are known in art for transmitting sound. The flexible tube 26 is attached to the connection port 48, such that there is no air exchange between the flexible tube 26 and the body 30, and such that the passageway through the tube 26 is in communication with the distal chamber 100 via the passageway 58 and aperture 56. When the earpiece 28 is inserted into the ears of the medical personnel, this allows substantially no air exchange between the cavity 50 of the microphone 22 and the outside the microphone 22. The length of the flexible tube 26 is adjusted so that maximum audible sound is received at the earpiece 28, which are used by medical personnel to hear the desired sounds in real time.

The combination of volumes V1 and V2 and the slot 104 around the preamplifier board 42 provide sufficient acoustic resistance for pressure equalization, and lowers the low frequency threshold. When the flexible tube 26 is connected to the earpiece 28, due to increased acoustic resistance and longer required period for pressure equalization, this lowers the low −3 dB frequency to 0.03 Hertz.

As described herein, the microphone may differ from U.S. Pat. No. 8,401,217 in that the body 30 is not completely sealed in that a connection port 48 is provided for connecting the microphone 22 to the flexible tube 26 and the earpiece 28, in that the preamplifier board 42 is mounted horizontally in the body 30 to divide the backchamber into two lower chambers 100 and 102 and that the preamplifier board 42 is parallel to the membrane 40, rather than being positioned vertically that is perpendicular to the membrane 40 as is positioned in U.S. Pat. No. 8,401,217, and in that the grid of U.S. Pat. No. 8,401,217 is eliminated and instead body 30 includes threads 54 for connection of the body coupler 24 or 24a to the distal end of the body 30.

Figure 5A:
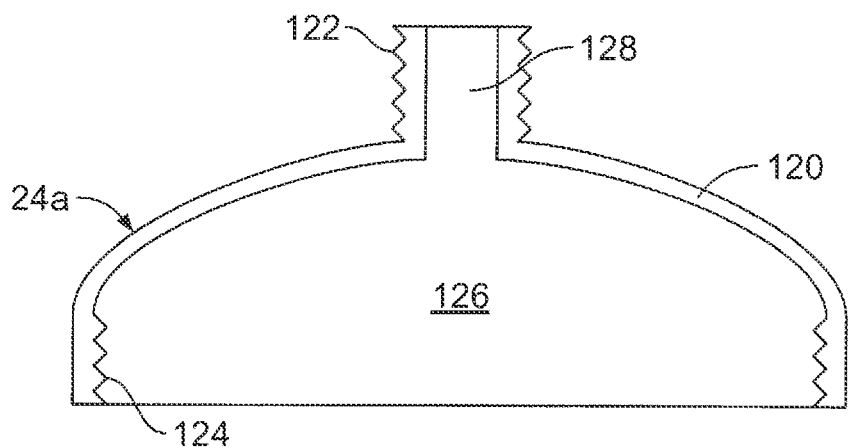
FIG. 5A is a cross-sectional view of a body coupler according to a second embodiment and which forms part of the infrascope of the present disclosure.

The body coupler 24, 24a threadedly attaches to the thread form 54 at the distal end of the body 30 such that there is no air exchange between the body coupler 24, 24a and the body 30. In one embodiment, as shown in FIG. 5, the body coupler 24 is formed of an outer ring 114 which has a flexible non-conductive diaphragm 116 attached thereto and which spans the diameter of the ring 114. The outer ring 114 may be formed either of thermoplastic polyurethane elastomers (TPU) or of closed cell polyurethane foam material which can be made of different densities, and has an internal thread form 118 for attachment of the outer ring 114 to the distal end of the body 30. The TPU material is used when full spectrum of acoustic signals are to be recorded from a heart and closed cell polyurethane foam material is used only when infrasonic signals is to be recorded as this material acts as a passive filter and audible sound is shunted off. When attached, the membrane 40 of the microphone 22 and the diaphragm 116 of the body coupler is approximately 0.1 inch apart. The body coupler 24 is placed against the body of the patient during the monitoring of the physiological process. In another embodiment, as shown in FIG. 5A, the body coupler 24a has a cup-like wall 120 having opposite proximal and distal ends and which defines a cavity 126 therein, and a connection port 122 extending from the distal end. The connection port 122 has a passageway 128 therethrough which is in fluid communication with the cavity 126 by an aperture 130 through the wall 120. The exterior surface of the connection port 122 may have a thread form thereon. The proximal end of the wall 120 is open and a thread form 124 is provided on the interior surface of the wall 120. The wall 120 and connection port 122 are formed either of aluminum or brass. With this second embodiment of the body coupler 24a, the proximal end of the flexible catheter tube 23 is attached to the connection port 122, and the thread form 124 engages with the thread form 54 on the body 30 of the microphone 22. As such, the connection between the catheter tube 23, the body coupler 24a and the microphone 22 is sealed to prevent air entrance therethrough. As is known, catheter tubes 23 have opening(s) 25 at the end of the tube 23. The end of the tube 23 may be inserted into the bladder 132 of a patient to provide internal fetal monitoring. The bladder 132 is proximate to the uterus 134 and sound, specifically infrasound, transmission is conveyed from the uterus 134, to the bladder 132, to the catheter tube 23 via the opening(s) 25, and then to the microphone 22.

As discussed herein, the preamplifier board 42 is installed parallel to the base wall 54 and to the membrane 24. The slot 104 between the edge of the preamplifier board 42 and the side wall 44 is small, for example 0.025", to increase acoustic resistance. The combined volumes V1 and V2 and the volume in the flexible tube 26 is 5×10−5 meter$^3$. Because of increased acoustic resistance, pressure equalization takes longer which aids in lower −3 dB frequency to 0.03 Hertz.

Figure 6:
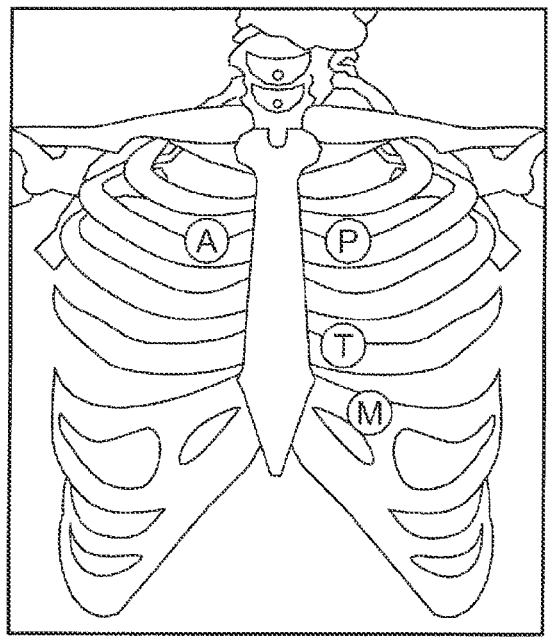
FIG. 6 is a schematic view of a skeleton of a patient.

In use, the body coupler 24 or catheter tube 23 detects incident sound pressure from the heart, the uterus, or from any other location of the body where it is placed. For example as shown in FIG. 6, the body coupler(s) 24 may be placed at locations A, P, T and/or M on the body of the patient. The sound pressure excites the motion of the membrane 40 within the microphone 22. The motion of the membrane 40 changes the capacitance between the membrane 40 and the backplate 38. This electrical signal travels from the backplate 38, through the conductor 36 and to the preamplifier board 42, thereby producing a proportional output voltage at the preamplifier board 42. The preamplifier board 42 is grounded via wire 112. The signal is sent from the preamplifier board 42 through the sealed electrical connection 106 to an electronics board which digitizes and transfers the data wirelessly to a nearby computer. The received signals are detected in the bandwidth of 0.03 through 1000 Hertz.

The microphone 22 provides damping of the motion of the membrane 40 for flat frequency response over a desired range by using the air gap 98 and the holes 92 in the backplate 38. When the membrane 40 vibrates, the membrane 40 compresses and expands the air layer in the air gap 98 and creates a reaction pressure, which opposes the motion of the membrane 40. The reaction pressure generates airflow which introduces damping primarily at two places: in the air gap 98 between the membrane 40 and the backplate 38, and in the holes 92 in the backplate 38 which provide large surface areas for viscous boundary layer damping.

As described in U.S. Pat. No. 8,401,217, in a 3 inch diameter infrasonic microphone 22, the tension of the membrane 40 may be less than about 1500 Newton per meter. For example, where the radius of the membrane 40 is about 0.0342 meter, the tension of the membrane 40 may be less than about 1000 Newton per meter. Further, the resonance frequency of the microphone 22 may be less than about 1000 Hertz. Still further, the volume of the backchamber may be selected to produce a low-frequency air compliance that exceeds the compliance of the membrane 40 by a factor of at least 3. In one example, the radius of the membrane 40 is about 0.0342 meter. In this example, the backplate 38 defines six holes 92, each having a radius of about 0.00302 meter. The holes 92 are evenly spaced along an imaginary circle on the backplate 38 and a center of each hole 92 is aligned with the imaginary circle. The center of the imaginary circle is located coincident with a center of the backplate 38, and the radius of the imaginary circle is about 0.0105 meter. The width of the slot 94 is about 0.0144 meter and the area of the slot 94 is about 0.00179 m$^2$.

In an approximately 1.5 inch diameter infrasonic microphone 22, where the radius of the membrane 40 is about 0.0134 meter, the tension of the membrane 40 may be less than about 400 Newton per meter. Further, the resonance frequency of the microphone 22 may be less than about 1500 Hertz. Still further, the volume of the backchamber may be selected to produce a low-frequency air compliance that exceeds the compliance of the membrane 40 by a factor of at least 10. In another example, the radius of the membrane 40 is about 0.0134 meter. In this example, the radius of each of the six holes 92 is about 0.002 meter and the radius of the imaginary circle is about 0.0117 meter. The width of the slot 94 is about 0.00351 meter and the area of the slot 94 is about 0.000258 m$^2$. The volume of the backchamber is about 0.00005 m$^3$.

Figure 7:
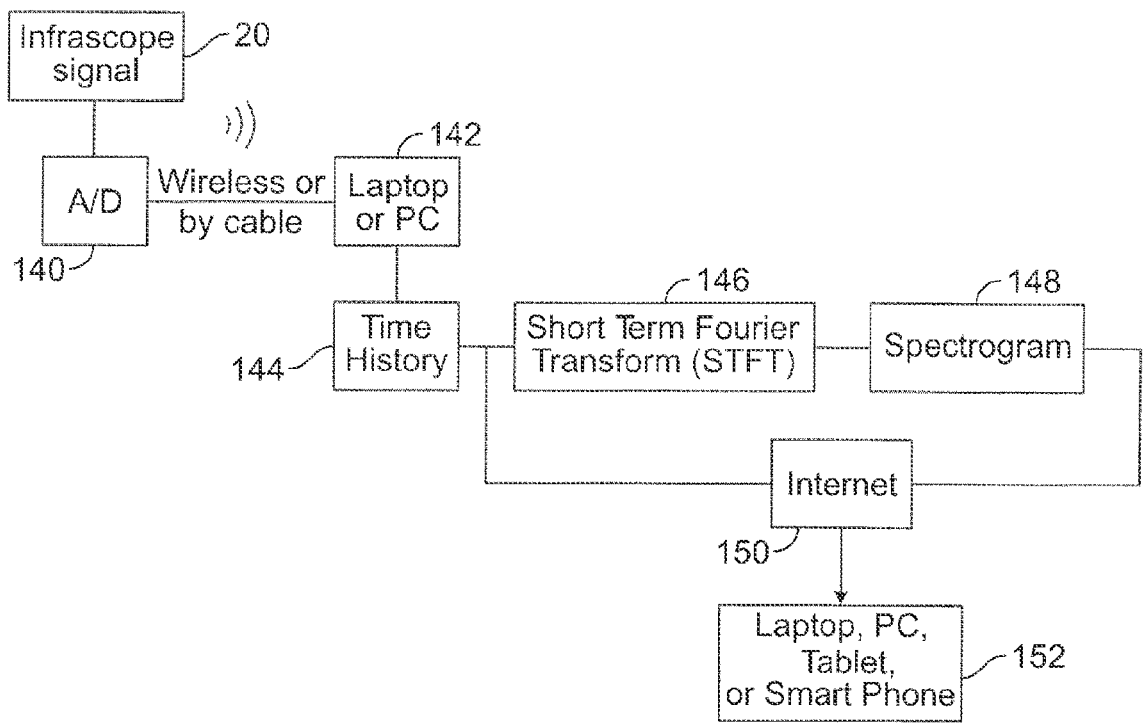
FIG. 7 is a flow chart regarding the process of how signals from the infrascope are transmitted and analyzed.
Figure 8:
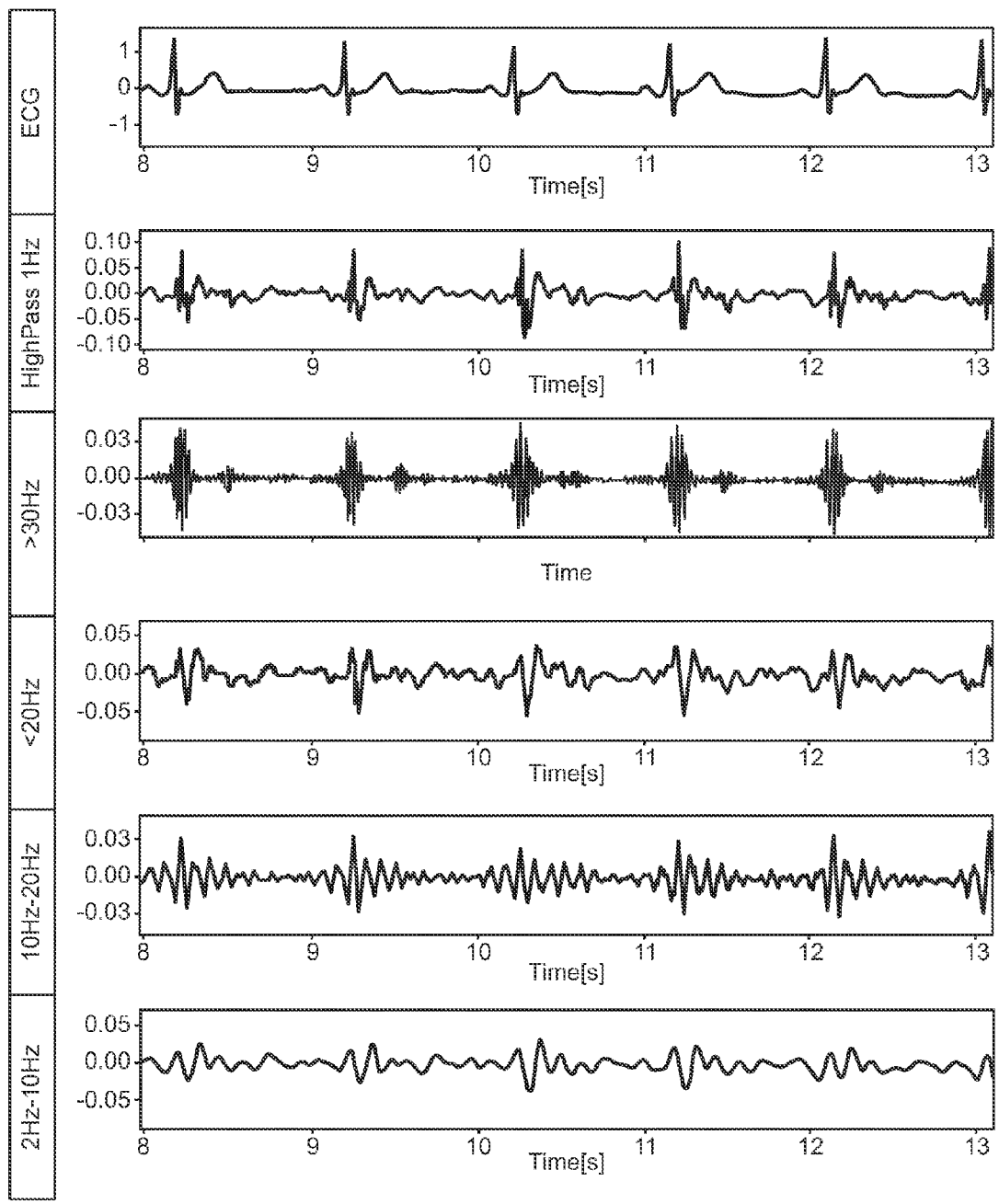
FIGS. 8-17 are charts of infrascope signals collected at locations A, P, T and M of FIG. 6 with reference to electrocardiogram signals referred as ECG or EKG.
Figure 9:
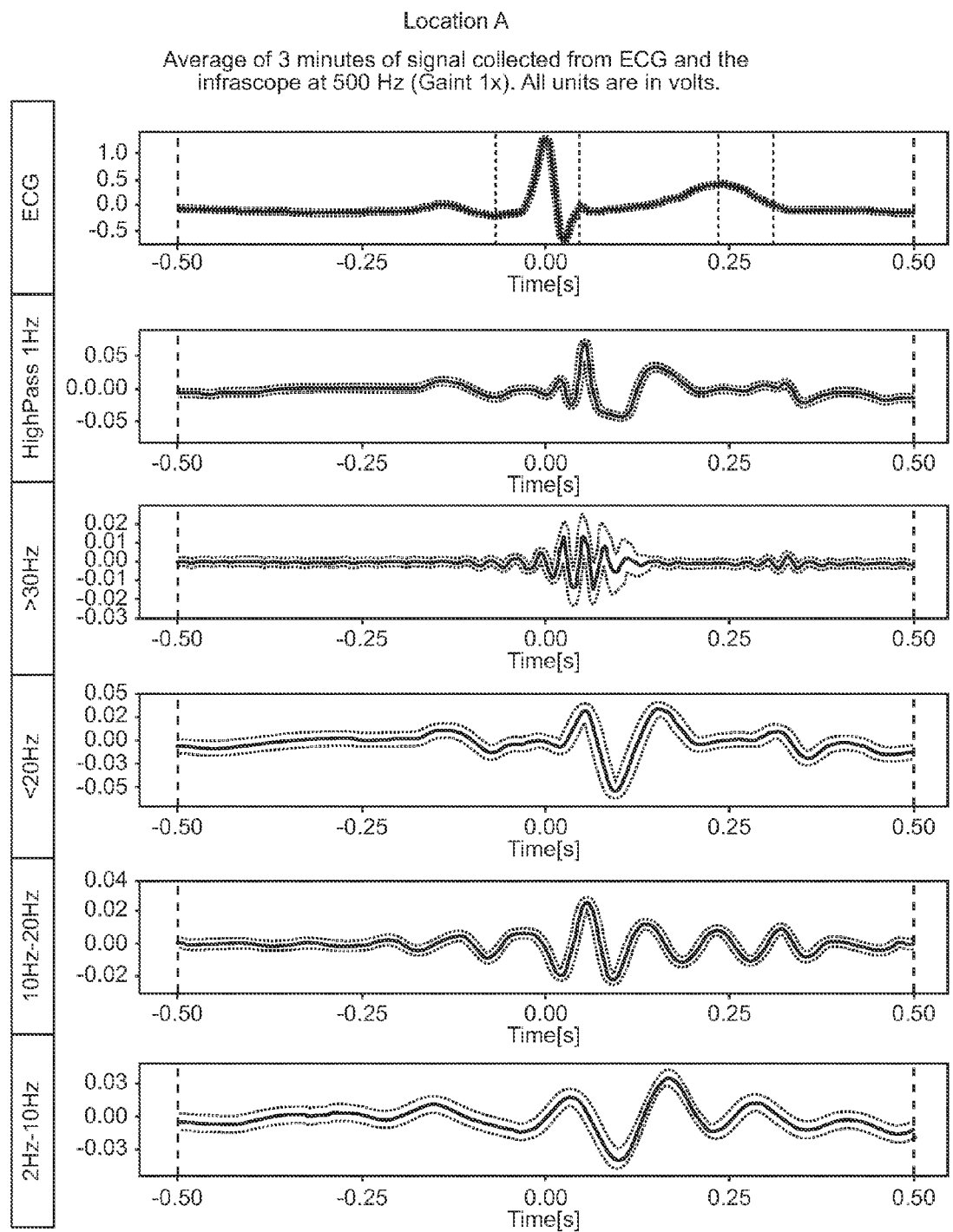
Figure 10:
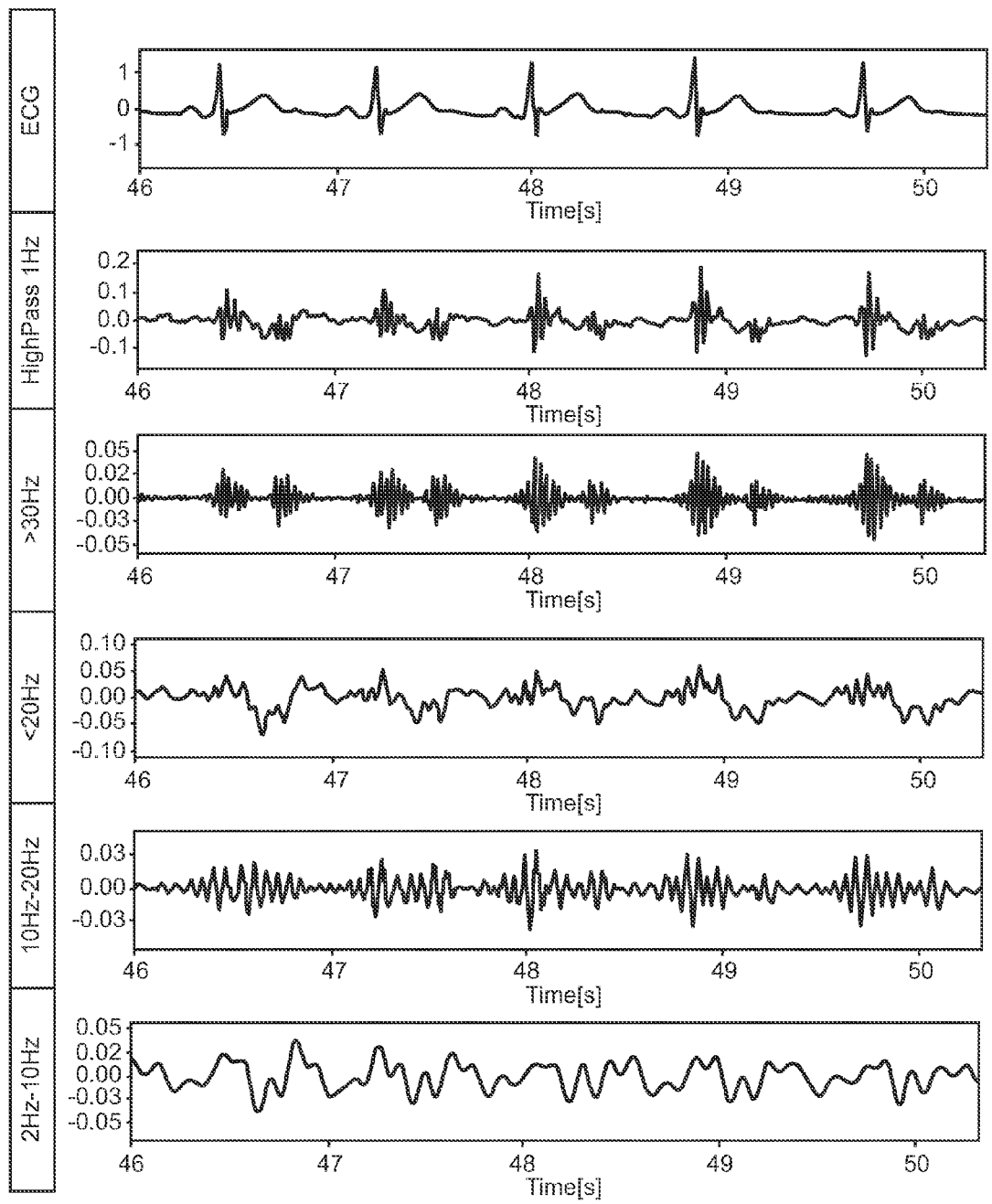
Figure 11:
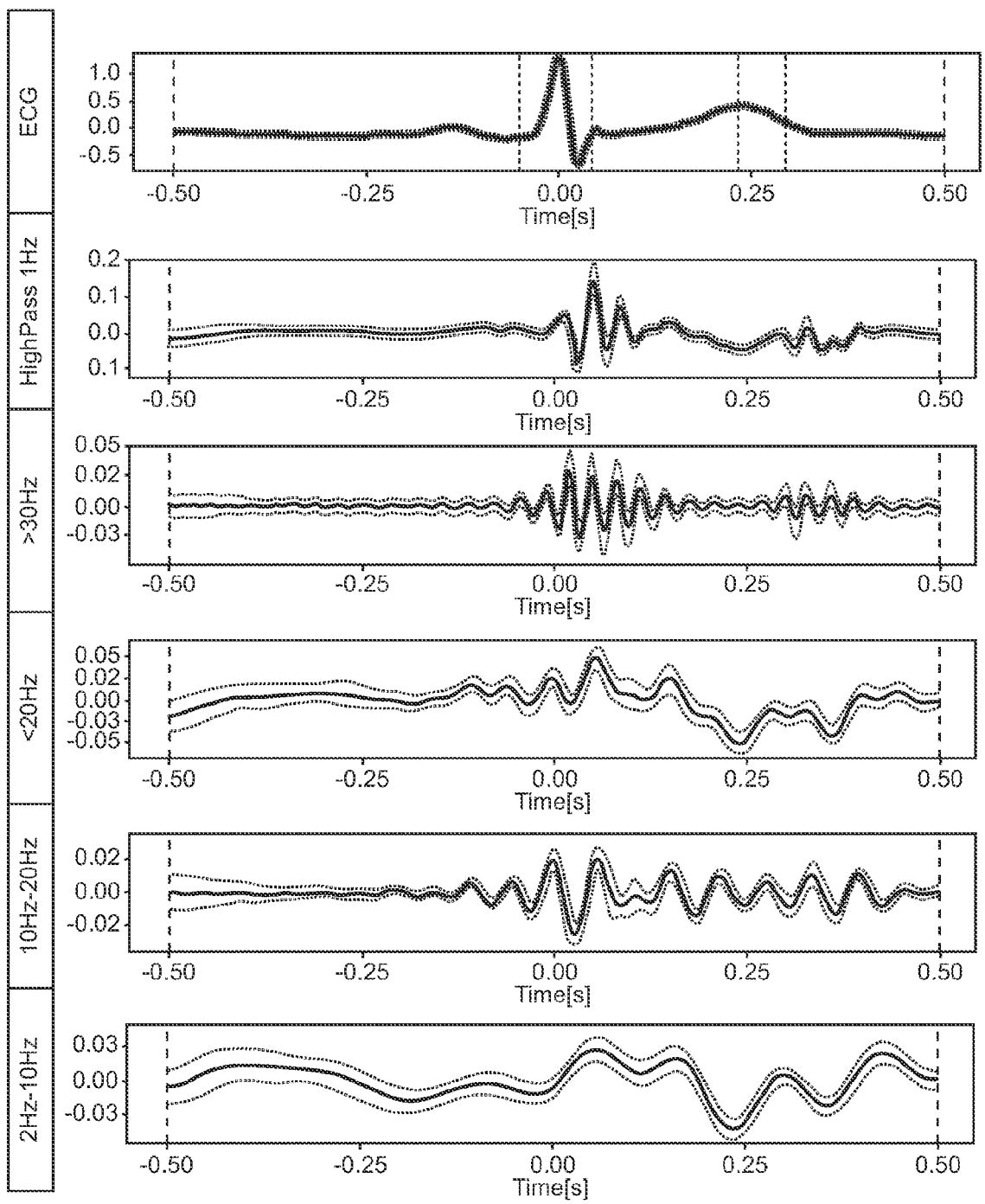
Figure 12:
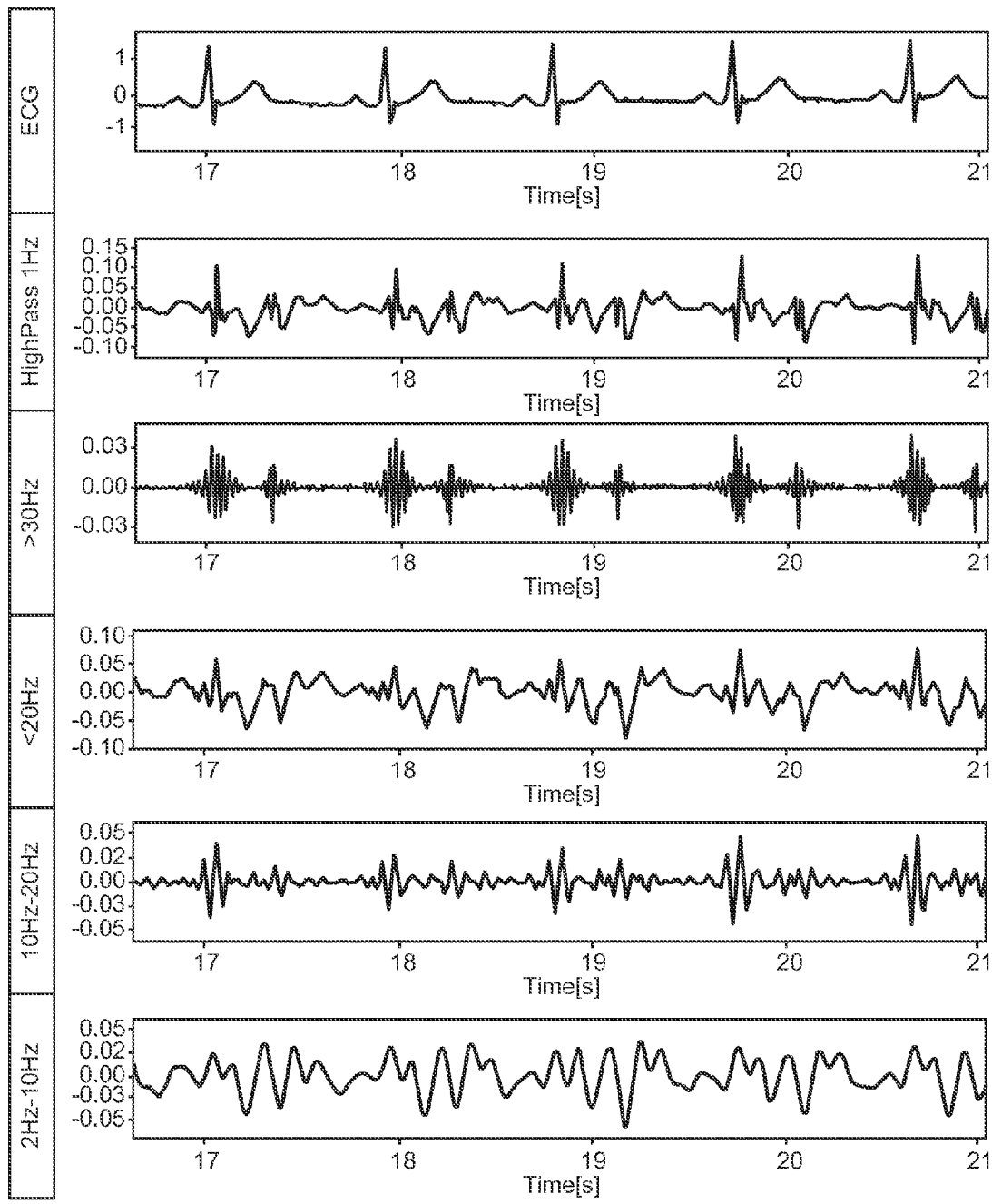
Figure 13:
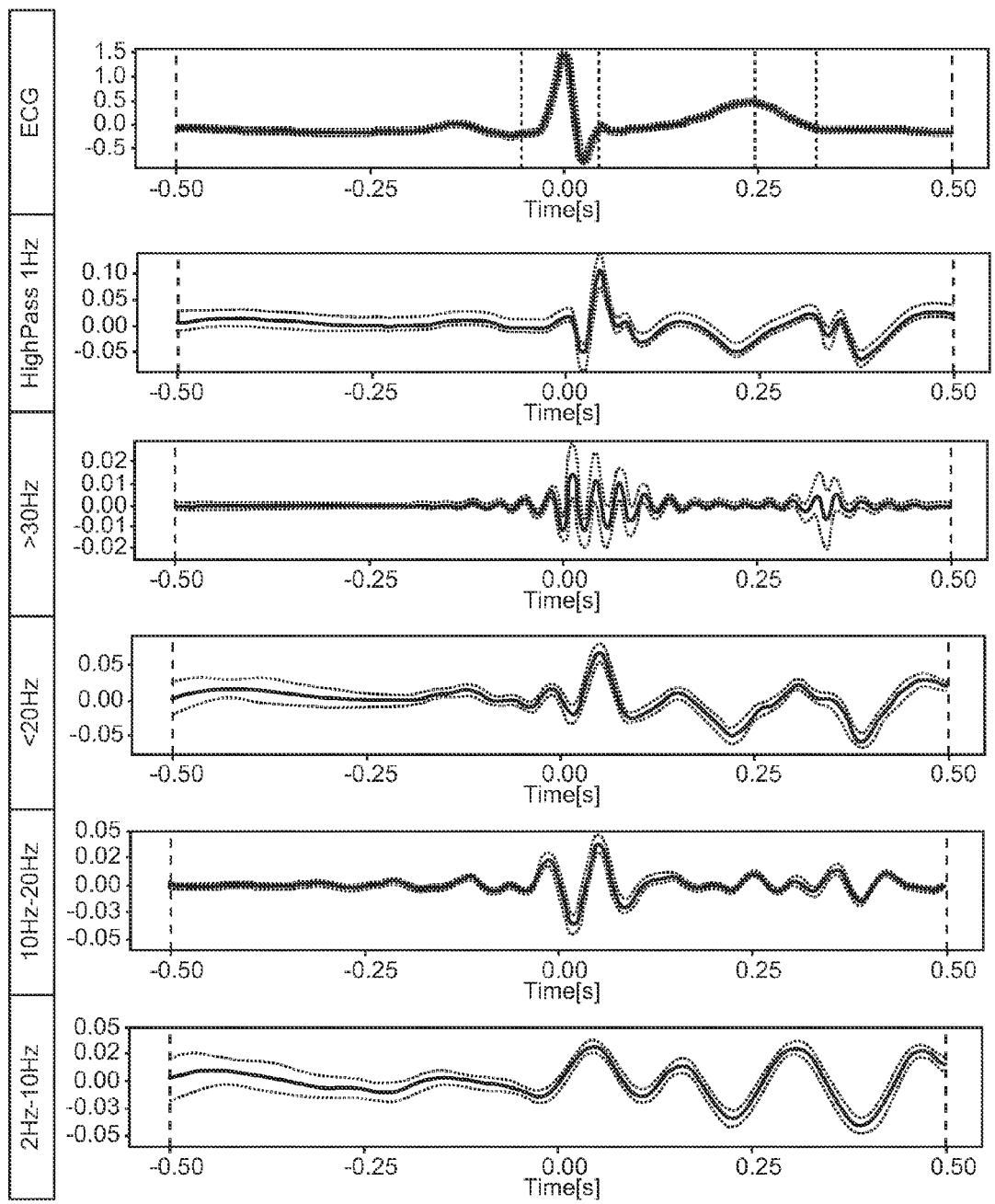
Figure 14:
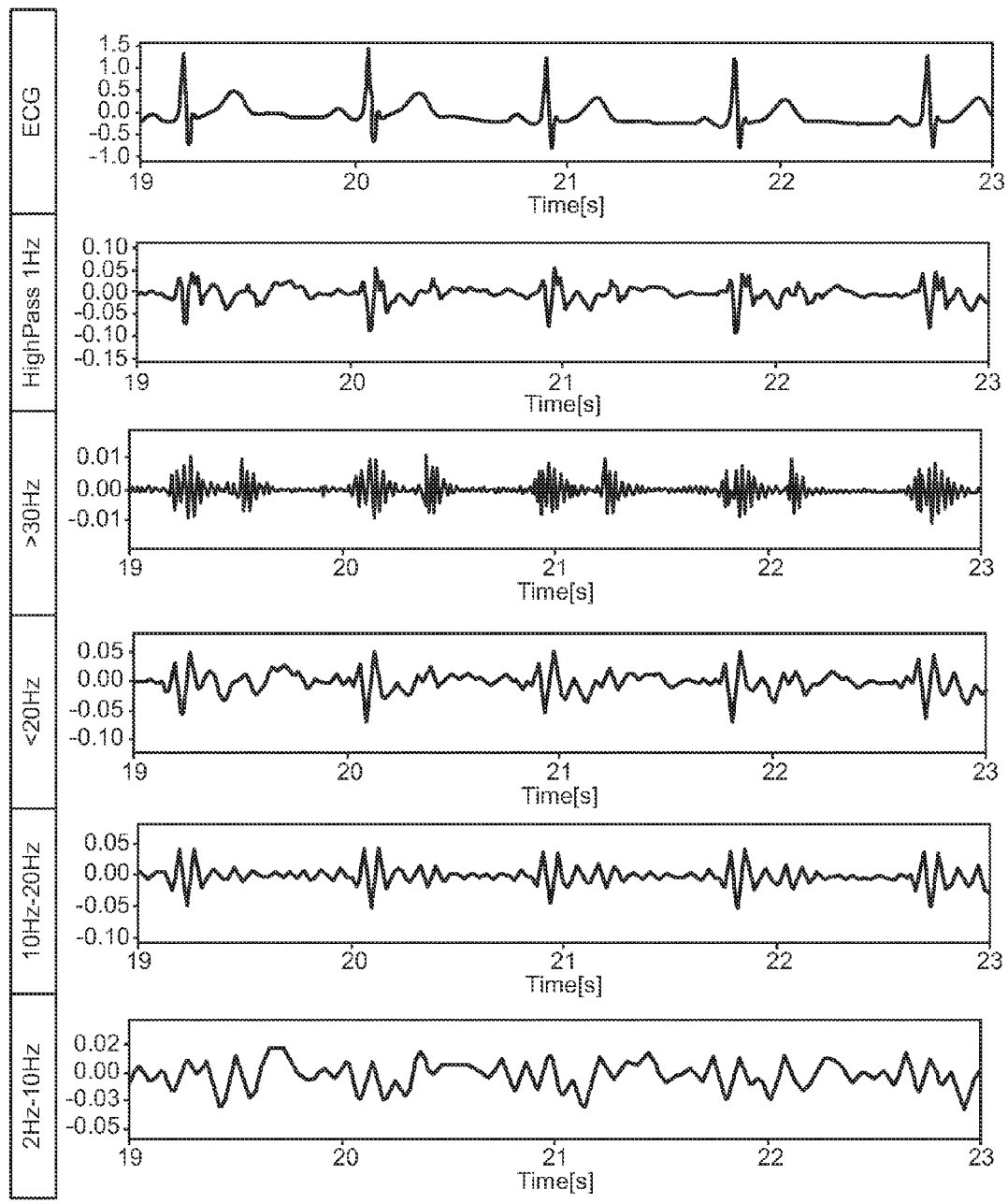
Figure 15:
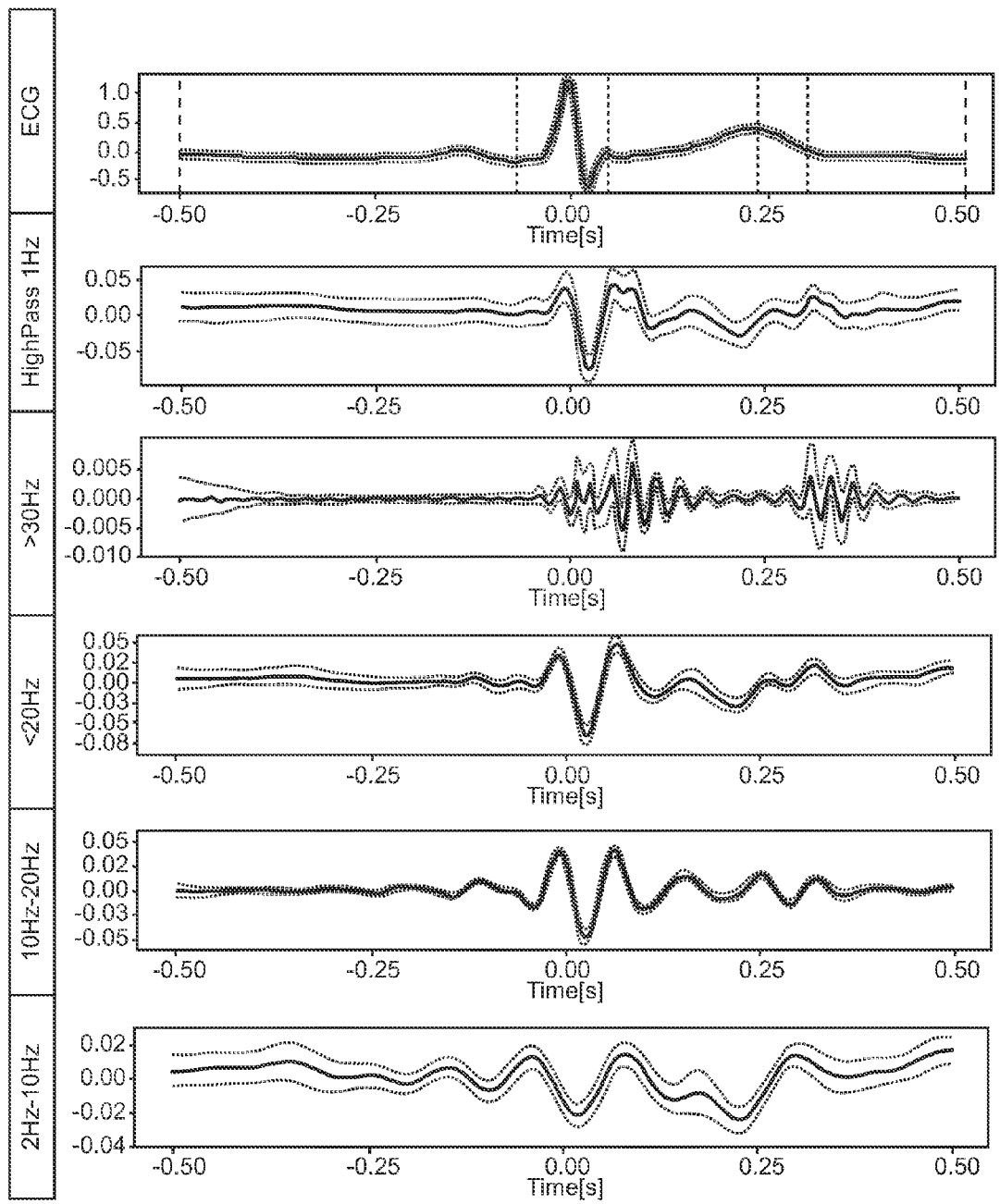
Figure 16:
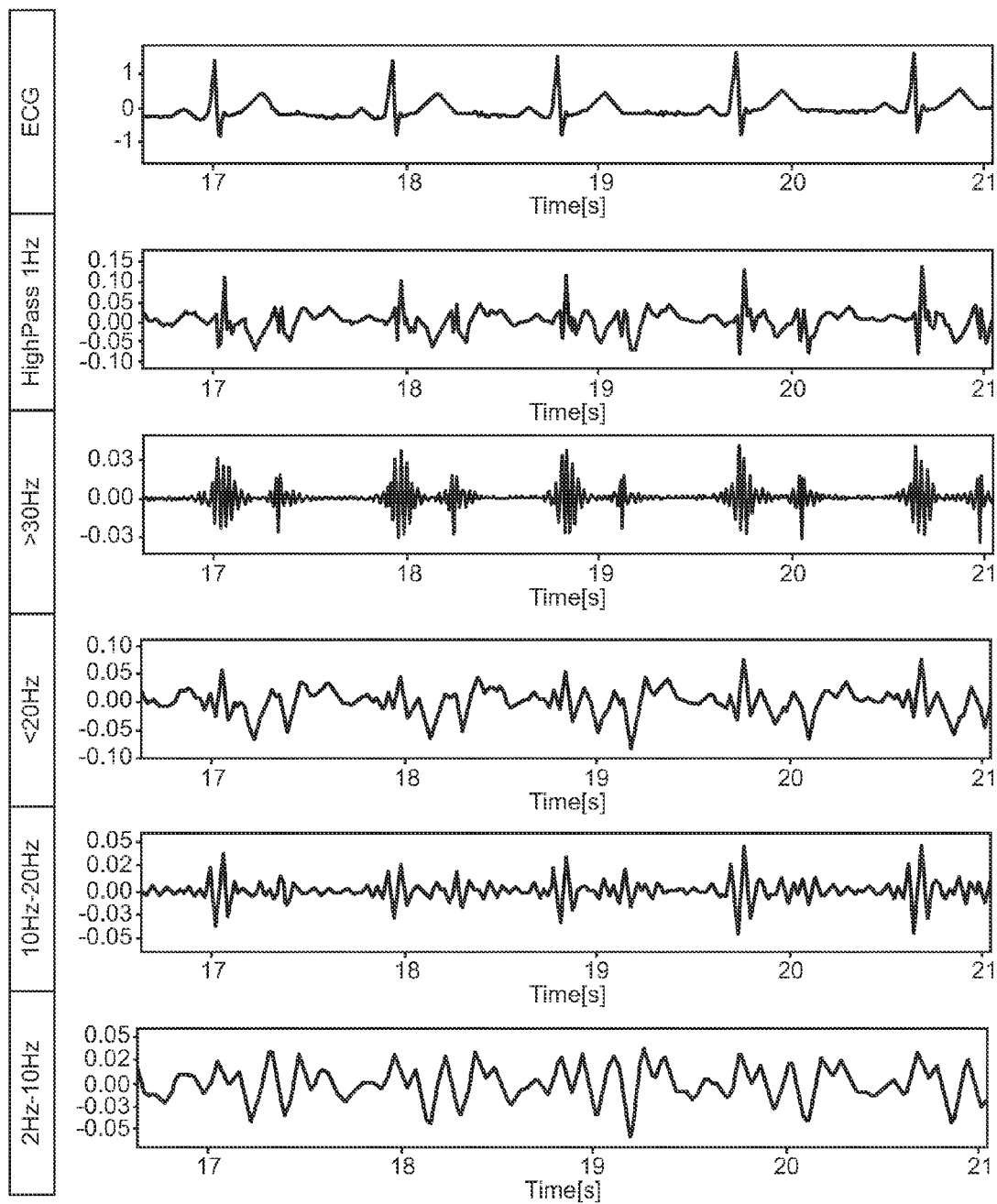
Figure 17:
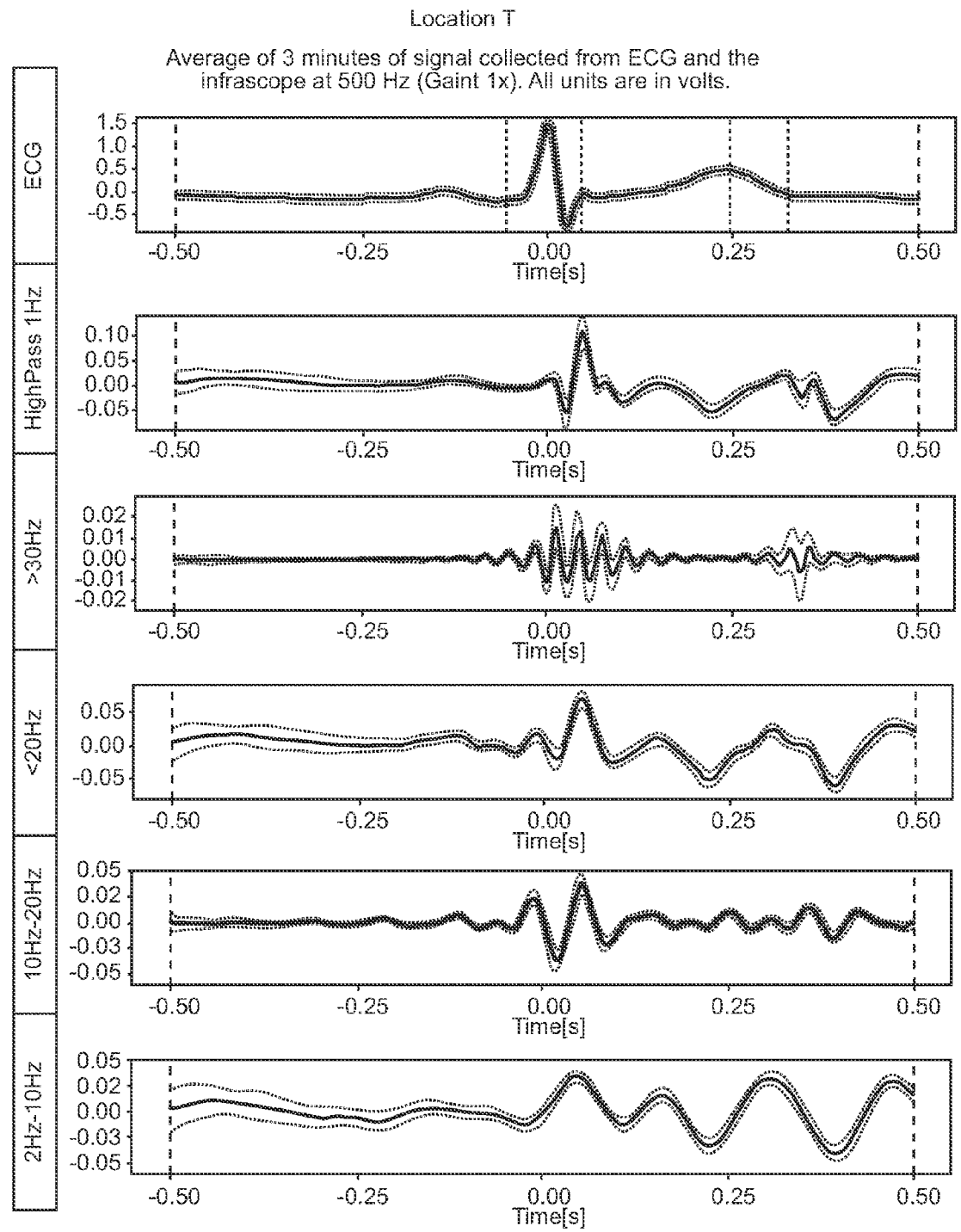

As shown in the block diagram of FIG. 7, the signals from the infrascope 20 are digitized via an analog to digital digitizer board 140. Once digitized, the signal is transmitted wirelessly or by cable to workstation 142, such as a laptop or personal computer. At 144, time history is plotted for data collected at different locations of the patient such as at locations A, T, P and M as shown in FIG. 6. The workstation 142 provides control, analysis and display of the recorded data. MATLAB may also be used to process the data to generate the real-time spectrograms using short-time Fourier transform (STFT) spectrum of the corresponding data at 146 and 148. The time history and spectrogram of biological signals is transferred by the Internet 150 to a remote workstation 152, if desired, for observation and analysis. Examples of such remote workstations 52 may be a remote computer monitor, smartphone or tablet. The signals may be sent via wired connection, or may be wirelessly transmitted, such as by using commercially available Bluetooth module, to PC or laptop for processing. The data is converted in useful visual format also called spectrogram, which may be helpful for physician to diagnose any abnormality. The display of short term spectra is performed in real time, in order to detect the presence of a short term event in the data.

Figure 18:
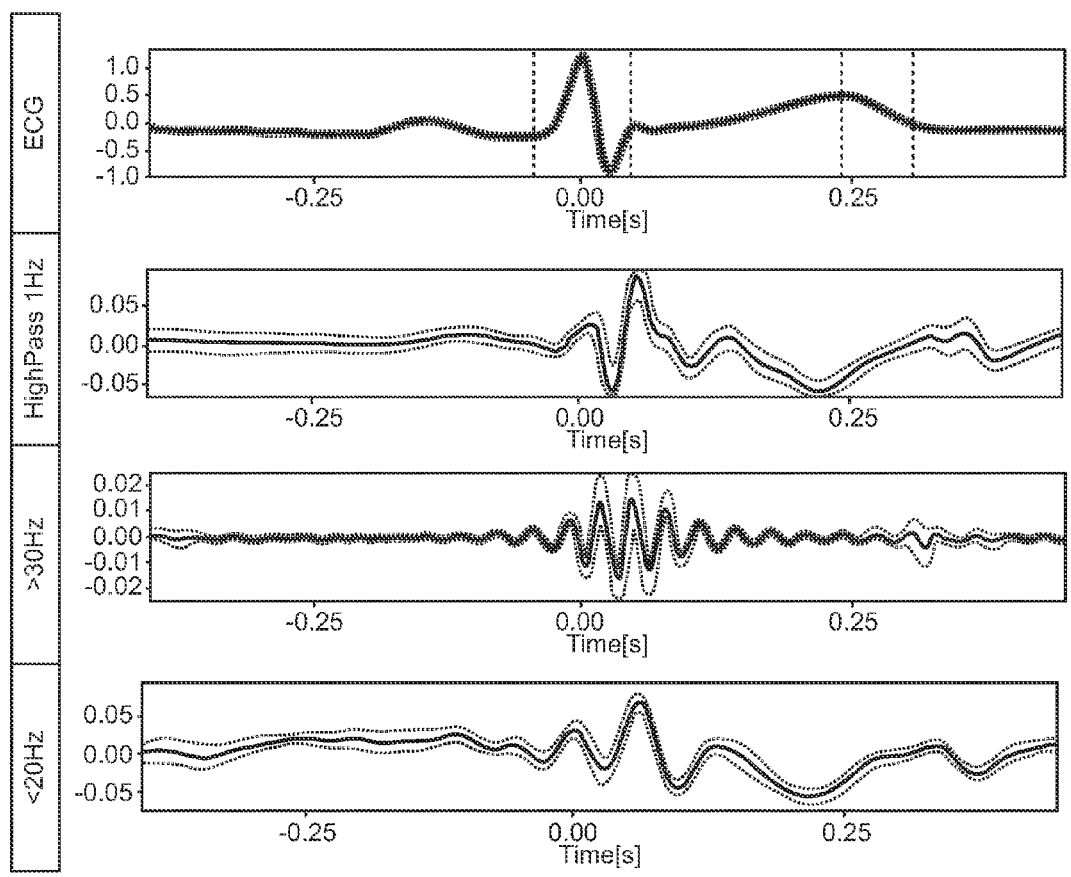
FIGS. 18 and 19 show charts of infrascope data as compared to ECG or EKG on two different subjects from 1 Hz through 1000 Hz.
Figure 19:
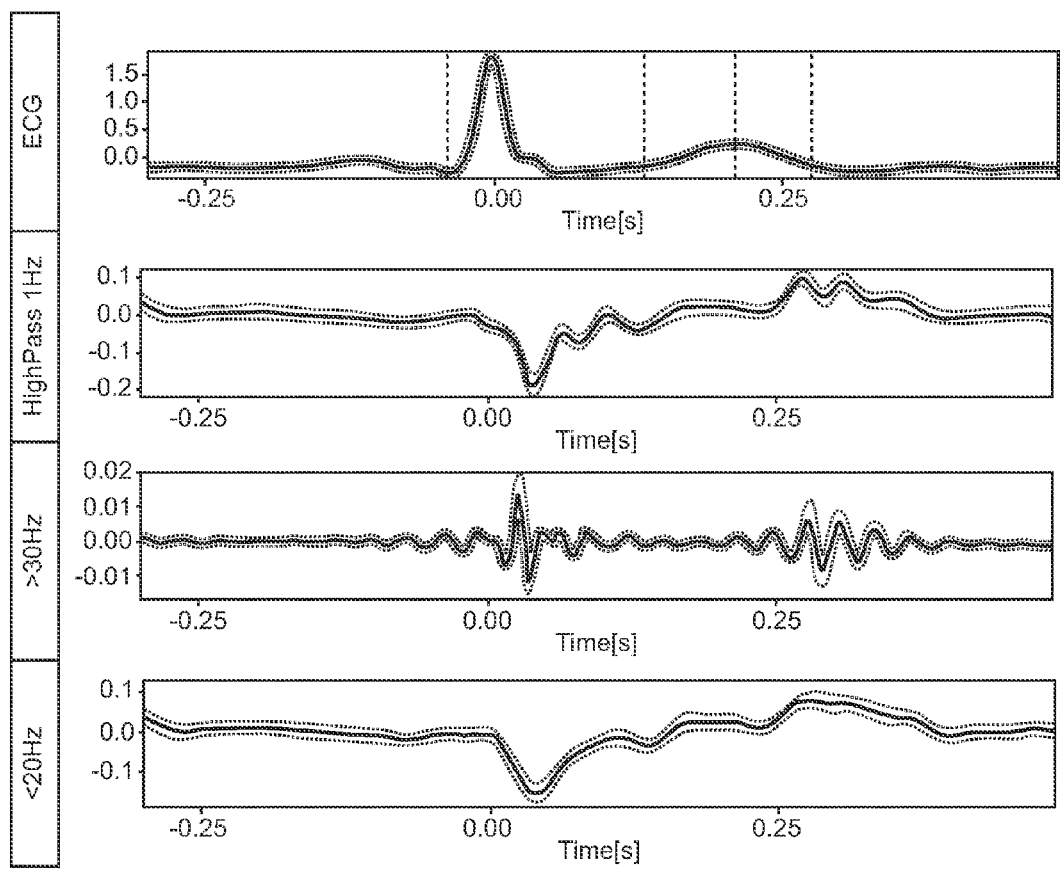

FIGS. 8-17 show charts of infrascope signals collected at locations A, P, T and M of FIG. 6 with reference to electrocardiogram signals usually referred as ECG or EKG. FIGS. 18 and 19 show charts of infrascope data as compared to ECG or EKG on two different subjects from 1 Hz through 1000 Hz. The ECG signals of both subjects are quite different and infrascope signals also follow the trend of ECG.

The infrascope 20 can be used for a stress phonocardiography test. Some heart problems occur only during physical activity. Stress phonocardiography test can be accomplished using the signals from the infrascope 20 immediately before and after walking on a treadmill or riding a stationary bike.

The infrascope 20 may be used for fetal heart monitoring during pregnancy, labor, and delivery to keep track of the heart rate of a fetus and the strength and duration of the contractions of uterus. External fetal heart monitoring which involves placing the body coupler 24 against the abdomen of the patient, keeps track of the baby's heart rate while at rest and while moving; measures the number of contractions and how long contractions last during labor and delivery; determines if there is preterm labor. Internal fetal heart monitoring, as shown in FIG. 2 and which uses the catheter 23 as described herein, determines if the stress of labor is threatening the baby's health; measures the strength and duration of the labor contraction.

Figure 3:
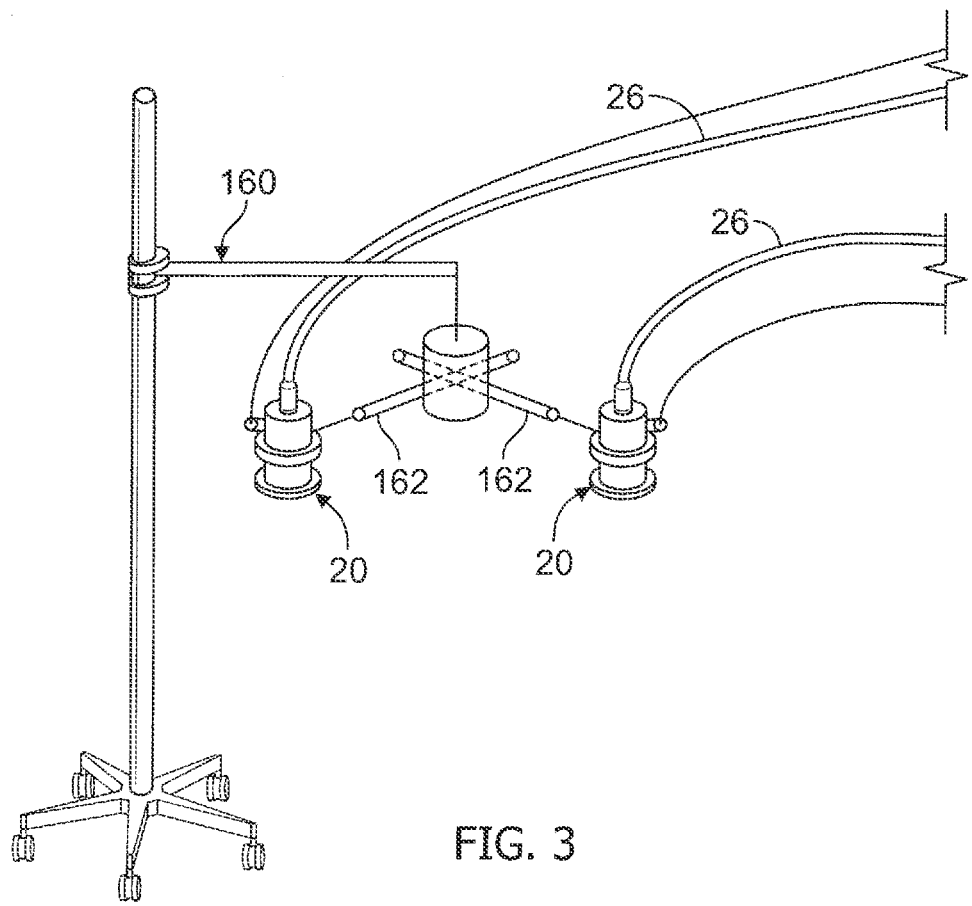
FIG. 3 is a perspective view of a pair of infrascopes which can be used in Doppler phonocardiography.

The infrascope 20 can be used for Doppler phonocardiography as shown in FIG. 3. A Doppler phonocardiography can be used to measure blood flow within the heart without an invasive procedure. The left ventricular filling pressure and blood flow can be estimated by using two infrascopes 20. The infrascopes 20 can be placed at any desired location, for example locations A, P, T and M, by using a mounting structure 160 having adjustable rods 162 attached to the microphones 22 to determine two dimensional velocity estimation and imaging.

The infrascope 20 can be used for biometric identification. Fingerprints have been used for identification for more than 100 years, but using heartbeat for biometric identification has some advantages such as convenience and security. The heartbeat signatures can be extracted using either ECG/EKG or by using the infrascope 20 at remote locations. The security feature is preserved from the fact that a user's ECG or acoustic signatures cannot be captured without a person's consent. Another disadvantage of fingerprints are that these can be replicated by using samples left behind. The infrasonic bandwidth signals provide better and higher signal to noise ratio values and another tool for biometric identification.

The infrascope 20 can be used for polygraphs. Physiological processes measured by polygraphs are; cardiovascular, electrodermal, and respiratory. The direction and extent of cardiovascular reactivity may be different across individuals in response to stimuli that may be considered arousing. Electrodermal activity in terms of skin resistance or conductance is measured by passing a current through the skin. In response to controlled and relevant questions, variations from basal levels are called electrodermal or EDR responses or electrodermal activity levels and is used for polygraph interpretation. Variations in respiration which also produce changes in heart rate and electrodermal activity is monitored to determine of responses to relevant and control questions are artifacts. Currently, the rate and depth of respiration during polygraph are measured by changes measured using strain gauges positioned on chest and abdomen. Extreme low frequency signal measurements can be made by positioning the infrascope 20 at a subject's chest and abdomen is a relatively inexpensive tool to measure variation in respiratory and cardiovascular activity.

The infrascope 20 of the present disclosure enables medical personnel to look at the audible bandwidth as well as infrasonic bandwidth, thus providing medical personnel with another tool to analyze physiological processes. The infrascope 20 can be used for respiratory, cardiac, and for fetal heart monitoring. The infrascope 20 enables physiological process signals to be transferred to any place in the world in real time. Ambulances can be equipped with the infrascope 20 and medical personnel are able to obtain a patient's physiological information in real time. The infrascope 20 is a relatively inexpensive tool to diagnose abnormality at early stage.

The terms "patient" is used throughout the disclosure, which includes humans and animals, as it is anticipated that the present invention would also be capable of monitoring physiological processes for veterinary practices.

All references disclosed herein are hereby incorporated by reference in their entirety.

While particular embodiments are illustrated in and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims.

What is claimed is:

1. A microphone for use in an infrascope for monitoring physiological processes of a patient, said microphone comprising:
   a body comprising a proximal end, a distal end, a body side wall extending between the proximal end and the distal end, an end wall at the proximal end, and an aperture at the distal end;
   a body coupler attached to the distal end and over the aperture so as to form a substantially air-tight seal, wherein the body coupler is capable of engagement with the patient;
   a cavity surrounded by the body side wall, the end wall and the body coupler;
   a conductive backplate within the cavity and defining a backchamber between the conductive backplate and the end wall;
   a conductive membrane within the cavity, the conductive backplate and the conductive membrane being spaced apart from each other to form a capacitor;
   a flexible diaphragm of the body coupler spaced apart from the conductive membrane, wherein acoustic energy is coupled through the flexible diaphragm and to the conductive membrane whereby movement of the conductive membrane changes a capacitance between the conductive membrane and the conductive backplate; and a preamplifier board in electrical connection with the conductive backplate, the preamplifier board (i) being capable of measuring the capacitance between the conductive membrane and the conductive backplate and converting the measured capacitance into a voltage signal, and (ii) being disposed toward the proximal end away from the conductive backplate, said microphone being capable of detecting acoustic signals in a frequency range of 0.03 Hertz to 1000 Hertz.

2. The microphone of claim 1, further comprising:

a conductive support plate attached to an internal surface of the body side wall within the cavity, the conductive support plate (i) comprising a base wall that divides the cavity into a distal chamber between the base wall and the distal end of the body and a proximal chamber between the base wall and the proximal end of the body, (ii) a base wall aperture within the base wall, and (iii) at least one aperture or slot within the base wall to allow air to flow from the distal chamber to the proximal chamber;

an insulating member extending through the base wall aperture in the conductive support plate;

a conductor extending through the insulating member and extending therefrom, the conductive member being electrically connected to the conductive backplate and to the preamplifier board, wherein the conductive backplate is on one side of the conductive support plate and the preamplifier board is on an opposite side of the conductive support plate.

3. The microphone of claim 1, wherein (i) the conductive backplate defines a plurality of holes, (ii) a slot is defined between an outer diameter of the conductive backplate and an inner wall of the body, and (iii) locations and sizes of the holes and a size of the slot are selected such that membrane motion is substantially critically damped.

4. The microphone of claim 3, wherein the conductive backplate is seated on the insulating member.

5. The microphone of claim 1, wherein a slot is defined between the preamplifier board and the body side wall, and extends around the preamplifier board.

6. The microphone of claim 1, wherein the preamplifier board defines a first proximal chamber between the preamplifier board and the end wall, and a second distal chamber between the preamplifier board and the base wall of the conductive support plate.

7. The microphone of claim 6, wherein the first proximal chamber has a volume of approximately 0.1287 cubic inch, and the second distal chamber has a volume of approximately 0.6 cubic inch.

8. The microphone of claim 1, wherein the body coupler is formed of an outer ring, the outer ring is attached to the body, and the flexible diaphragm is attached to the outer ring.

9. The microphone of claim 1, further comprising a sealed electrical connection extending though the body side wall, said sealed electrical connection enabling electrical connection of said microphone to an electronics board.

10. The microphone of claim 1, further comprising a digitizer board which is remote from the microphone, said digitizer board being capable of digitizing the voltage signal from the preamplifier.

11. The microphone of claim 1, wherein the voltage signal is digitized and electronically transmitted to a remote location.

12. An infrascope for monitoring physiological processes of a patient, said infrascope comprising the microphone of claim 1.

13. A method of using the microphone of claim 1, said method comprising:

positioning the microphone to detect sound pressure from one or more locations within a patient's body.

14. A method of using two microphones of claim 1, said method comprising:

positioning the two microphones to detect sound pressure from one or more locations within a patient's body.

15. A method of using the microphone of claim 1, said method comprising:

generating a physiological process signal from detected sound pressure from one or more locations within a patient's body within a frequency range of 0.03 Hertz to 1000 Hertz, the physiological process signal being transmittable in real time.

16. A method of using the microphone of claim 1, said method comprising:

generating a digitized signal from detected sound pressure from one or more locations within a patient's body within a frequency range of 0.03 Hertz to 1000 Hertz, the digitized signal being transmittable to a remote workstation.

17. A method of using the microphone of claim 1, said method comprising:

generating a digitized signal from detected sound pressure from one or more locations within a patient's body within a frequency range of 0.03 Hertz to 1000 Hertz, the digitized signal being transmittable to a remote workstation comprising a laptop computer, a personal computer, a remote computer monitor, a smartphone, or a tablet.

18. A method of using the microphone of claim 1, said method comprising:

using the microphone in (i) a stress phonocardiography test, (ii) for fetal heart monitoring during pregnancy, labor and delivery, (iii) for Doppler phonocardiography, (iv) for biometric identification, or (v) for polygraphs.

19. A method of using the microphone of claim 1, said method comprising:

using the microphone to at least one of generate a spectrogram and monitor respiratory, cardiac, or fetal heart physiological processes.

20. A microphone for use in an infrascope for monitoring physiological processes of a patient, said microphone comprising:

a body comprising a proximal end, a distal end, a body side wall extending between the proximal end and the distal end, an end wall at the proximal end, and an aperture at the distal end;

a body coupler attached to the distal end and over the aperture so as to form a substantially air-tight seal, wherein the body coupler is capable of engagement with the patient;

a cavity surrounded by the body side wall, the end wall and the body coupler;

a conductive backplate within the cavity and defining a backchamber between the conductive backplate and the end wall;

a conductive membrane within the cavity, the conductive backplate and the conductive membrane being spaced apart from each other to form a capacitor;

a preamplifier board in electrical connection with the conductive backplate, the preamplifier board (i) being capable of measuring a capacitance between the conductive membrane and the conductive backplate and converting the measured capacitance into a voltage signal, and (ii) being disposed toward the proximal end away from the conductive backplate; and air passages disposed at different levels in the microphone for airflow from the distal end to the proximal end of the body, said microphone being capable of detecting acoustic signals in a frequency range of 0.03 Hertz to 1000 Hertz.

\* \* \* \* \*